US005893070A

United States Patent [19]
Garber et al.

[11] Patent Number: 5,893,070
[45] Date of Patent: Apr. 6, 1999

[54] SYSTEM AND METHOD FOR DEVELOPING AND/OR MAINTAINING A WORKPLACE RESPIRATORY PROTECTION PROGRAM

[75] Inventors: Sharon R. Garber, Crystal; Craig E. Colton, Stillwater, both of Minn.; David S. Lucas, Mt. Elgin, Canada

[73] Assignee: Minnesota Mining and Manufacturing Co., St. Paul, Minn.

[21] Appl. No.: 659,022

[22] Filed: Jun. 4, 1996

Related U.S. Application Data

[63] Continuation of Ser. No. 233,589, Apr. 26, 1994, abandoned.

[51] Int. Cl.$^6$ .......................... G06F 159/00; G06F 17/40; G06F 17/60
[52] U.S. Cl. ................................ 705/2; 707/1; 707/501; 707/505
[58] Field of Search ................................ 705/1, 2, 3, 4, 705/7, 8; 707/104, 1, 102, 501, 505, 506, 507, 508; 600/300

[56] References Cited

U.S. PATENT DOCUMENTS

| | | | |
|---|---|---|---|
| 4,347,568 | 8/1982 | Giguere et al. | 600/300 |
| 5,241,671 | 8/1993 | Reed et al. | 395/600 |
| 5,251,294 | 10/1993 | Abelow | 395/155 |
| 5,265,247 | 11/1993 | Wienck et al. | 707/104 |
| 5,303,575 | 4/1994 | Brown et al. | 73/23.3 |
| 5,341,469 | 8/1994 | Rossberg et al. | 707/514 |

OTHER PUBLICATIONS

Kirkwood et al; "Sarah: An expert system . . . ", *Ann Occ. Hyg.*, Apr., 1991, 35(2), pp. 233–237 (Dialog Journal Announcement).

Smith, S.L.: "Keep the shine on your respirator program.", *Occupational Hazards*, vol. 54, No. 11, p. 34, Nov. 1992.

Author not known: "Worker safety hinges on knowledge", *Plant Engineering*, vol. 47, No. 5, p. T–12, Mar. 18, 1993.

Henry, Mike: "For environmental contractors, protective gear . . . ", *American Agent & Broker*, vol. 66, No. 4, pp. 22–23, Apr. 1994.

Dialog File 15, Acc. No. 00723454; "Hazard Awareness Health and Safety Library: Multimedia Interactive Learning on CD–ROM" by Nancy E. Bernal; *CD–ROM Professional*, v. 5; n.1, pp. 92–97, Jan. 1992.

Dialog File 151, Acc. No. 0211899; "Designing a Respirator Fit Testing Program". D.C. Murphy, *AAOHN J* (United States) 40(11), pp. 545–548 [Abstract only], Nov. 1992.

Dialog File 621, Acc. No. 00352936; News Release: "OSHA–Soft, Inc. Releases Fast Regs/ADA" Keene, NH, Feb. 23, 1993.

Toppila, et al., "Noise Scan—An Expert System with Multiple Areas of Expertise," Research to Prevention. Managing Occupational and Environmental Health Hazards, People and Work. Research Reports 4, Proceedings of the International Symposium, 20–23 Mar., 1995, Helsinki, Finalnd, J. Rantane, 1995.

(List continued on next page.)

*Primary Examiner*—Joseph Thomas
*Attorney, Agent, or Firm*—Marshall, O'Toole, Gerstein, Murray & Borun

[57] ABSTRACT

A respiratory program is disclosed which fully integrates the development and maintenance of a workplace respiratory protection program. The respiratory program (i) provides the forms which are useful in developing and maintaining a workplace respiratory protection program, (ii) facilitates the training of employees which is necessary to ensure that the workplace respiratory protection program is effective, (iii) includes the database which is necessary to provide all of the knowledge required during the development and maintenance of a workplace respiratory protection program, (iv) permits customization of the workplace respiratory protection program, (v) allows the employer and employees to read the knowledge provided by a fully informative workplace respiratory protection program, and (vi) assists the employer in preparing for an audit of the workplace respiratory protection program.

58 Claims, 38 Drawing Sheets

OTHER PUBLICATIONS

"Software Reviews", by Neil T. McManus, CIH, ROH, Deparment Editor, Am. Ind. Hyg. Assoc., J. (56) / Jun. 1995.

Administrative Respiratory Protection Program Written Standard Operating Procedures, pp. 2–13.

Manual Relating To Administrative Respiratory Protection Program Written Standard Operating Procedures and released by 3M.

Brochure—Software 2000, The AS/400 Software Market Survey by Sentry Market Research (6 pages), 1992.

Brochure—Medgate OHS&E Software Article, AIHCE May 1993.

Brochure—Stewart–Todd Corporate Maintenance Subsystem.

Brochure—O.R.M. Objective Risk Management.

Brochure—RegScan "We Gotta Talk".

Brochure—SSG, WARE: The Worksite Accident Reduction Expert, Systems & Software Group.

Brochure—RespFit, Respirator Fit Testing Software, SIGMA Science.

Brochure—OHMIS, Occupational Health Management Information System "HEARS HHIM MIM".

Brochure—ChemAdvisor, Inc. Regulatory Compliance Products & Services.

Brochure—Industrial Hygiene Specialty Services, Exposure Base Software.

Brochure—"We don't make the rules. We just make them easier for you to find.", Micromedex, Inc., IHS.

Brochure—OSHALOG.200 Series, Risk Management Software Solutions for Business and Industry, Safety Software.

Brochure—Employee Health Environmental Surveillance Regulatory Compliance, Flow Gemini, Occupational Health and Environmental Information Systems.

Brochure—"How to obtain Regulatory relief. In seconds.", OSHA–Soft, Inc.

Brochure—Environment Today, Special Supplement to Environmental Technology News, Software spotlight: Compliance programs prove their worth, ERM Computer Services, Inc., Jan., 1993.

Brochure—SuperTrak Occupational Health Information Tracking System.

```
┌─Welcome to Comply─────────────────────┐
│                                   ┌─┐ │
│                                   └─┘ │
│                                       │
│  What is today's date [mm/dd/yy]? 04/11/94
│                                       │
│  Do you want help getting started? Y ──302
│                      (Y or N)         │
│                                       │
│              Accept                   │
└───────────────────────────────────────┘
          300
```

FIGURE 3

```
┌─Getting Started Help──────────────────┐
│                                   ┌─┐ │
│                                   └─┘ │
│ Select F1 at any time to get Help.    │
│                                       │
│ The following screen (Getting Started) lists items which should be
│ completed when setting up a respirator program. Fill out as much as
│ possible in the order indicated.      │
│                                       │
│ After completing the Getting Started screen, items can be viewed or
│ modified from the Main Menu Screen.   │
│                                       │
│                   OK                  │
└───────────────────────────────────────┘
       400
```

FIGURE 4

―――― Customized Program Information ――――

Standards Preferred:   ( ) U.S. (OSHA)        ( ) Canadian (CSA)

In addition to air purifying respirators (negative and
positive pressure), which of the following are in use at
this site? Check all which apply.

Atmosphere Supplying (Airline
   or SCBA)                          [ ]

Escape Only Respirator            [ ]

Emergency Use Respirator          [ ]

[Print]   [Done]

[Next Page]   [Previous Page]   [Go to Main]

[F1] - help. Select fields with tab / shift-tab.

Select Respirators: [a/a]

| √ | Type | Model | Co |
|---|---|---|---|
| | Acid Gas | 5000 | 3M |
| | Acid Gas | 6000 | 3M |
| | Acid Gas | 7000 | 3M |
| | Acid Gas W/Dust/Mist | 7000 | 3M |
| | Acid Gas W/Dust/Mist (2020 filter) | 5000 | 3M |
| | Acid Gas W/Dust/Mist (2020 filter) | 6000 | 3M |
| | Acid Gas W/Dust/Mist (5010 prefilter) | 6000 | 3M |
| | Acid Gas W/Dust/Mist (5010 prefilter) | 5000 | 3M |
| | Acid Gas W/HEPA | 5000 | 3M |
| | Acid Gas W/HEPA | 6000 | 3M |
| | Acid Gas W/HEPA | 7000 | 3M |
| | Ammonia/Methylamine | 5000 | 3M |

Use Tab, Arrow Keys, or Mouse to Scroll to Right for more respirator Info

Search field: TYPE
Search for:

Multiple Select

| Accept | F2 | Cancel | Esc | Select | Enter | Add | Ins |
| Search | F5 | Again | Alt-F5 | | | | |

FIGURE 10

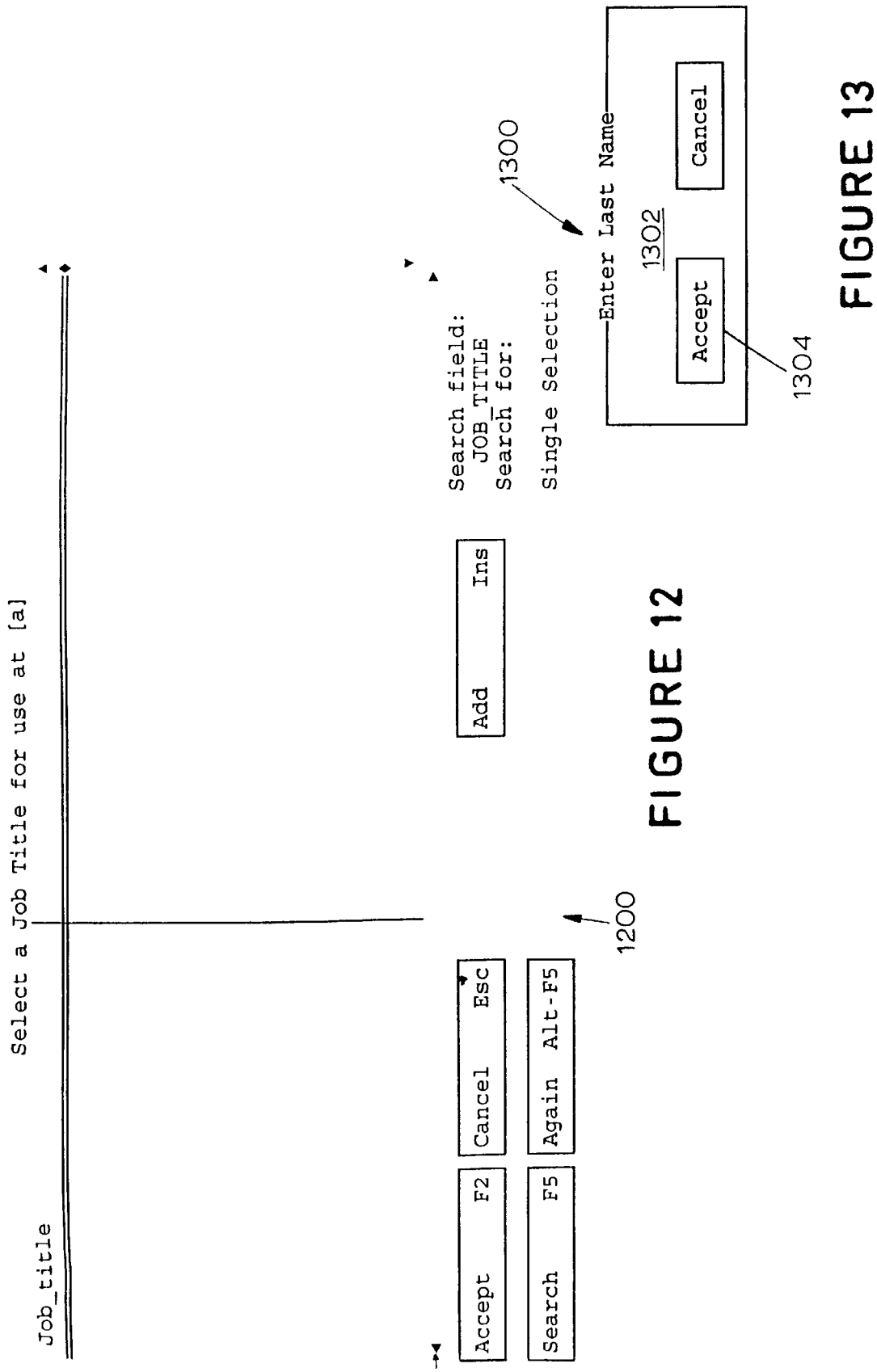

FIGURE 14

| Location | Job_title | Select Location/Job/Respirator Company | Model | Type |
|---|---|---|---|---|
| a | a | 3M | 5000 | Acid Gas |

Use Tab, Arrow Keys, or Mouse to Scroll to Right for more respirator Info

| Accept | F2 | Cancel | Esc |
|---|---|---|---|
| Search | F5 | Again | Alt-F5 |

Search field:
  LOCATION
Search for:
  Single Selection

Respirator Training Program Attendance Roster

Date:
[mm/dd/yy]

Company Name:
Address:

Program Adm:
Trainer:

Respirator —1602    1604

Name —1606

1608

Delete Record    Print    Go Back    Go to Main

[F1] - help. Select fields with tab / shift-tab.

```
┌─────────────────────────────────────────────────────────────┐
│ ─────── Medical Questionnaire (1/3) ───────             ▄▄  │
│                                                              │
│ Name:                                                        │
│ Employee ID/SSN:                  Date [mm/dd/yy]:          │
│                                                              │
│ Company Name:                                                │
│ Supervisor:                                                  │
│                                                              │
│ Birth Date [mm/dd/yy]:  /  /      Height:  0.0   Weight: 0.0│
│                                                              │
│ Have you ever worn a respirator before?  ( ) Yes   ( ) No   │
│                                                              │
│ If yes, describe any apparent difficulties noted with        │
│ respirator use:                                              │
│                           ↑2202                              │
│                                                              │
│                                         ┌──────────────┐    │
│                                         │     Done     │    │
│  ┌───────────┐        ┌───────────────┐ ├──────────────┤    │
│  │ Next Page │        │ Delete Record │ │  Go to Main  │    │
│  └───────────┘        └───────────────┘ └──────────────┘    │
│       2204                   2206             Print         │
│                                                              │
│  [F1] - help. Select fields with tab / shift-tab.           │
└─────────────────────────────────────────────────────────────┘
                              2200

FIGURE 22
```

```
┌─────────────── Medical Clearance (1/3) ───────────────┐
│                                                        │
│ Name:                             Date [mm/dd/yy]: / / │
│ Employee ID/SSN:          Date of Birth [mm/dd/yy]: / /│
│ Department:                                            │
│ Supervisor:                                            │
│ Check type or types of respirator(s) to be used:       │
│ [ ] Air-Purifying (nonpowered)                         │
│ [ ] Air-Purifying (powered)                            │
│ [ ] Continuous-Flow Air-Line Respirator                │
│ [ ] Pressure Demand Air-Line Respirator                │
│ [ ] Combination Continuous-Flow Air-Line and Air-Purifying Respirator │
│ [ ] Combination Pressure Demand Air-Line and Air-Purifying Respirator │
│ [ ] Combination Air-Line and SCBA                      │
│ [ ] Open circuit SCBA                                  │
│ [ ] Closed circuit SCBA                                │
│ Select Level of Work Effort                            │
│ ( ) Light                  ──────2302                  │
│ ( ) Moderate                                           │
│ ( ) Heavy                                              │
│ ( ) Strenuous                                          │
│ ┌──────────┐         ┌──────────────┐  ┌───────┐ ┌──────┐│
│ │Next Page │         │Delete Record │  │ Print │ │ Done ││
│ └──────────┘         └──────────────┘  └───────┘ └──────┘│
│                                                ┌────────────┐│
│     [F1] - help. Select fields with tab / shift-tab. │Go to Main││
│                                                └────────────┘│
└────────────────────────────────────────────────────────┘
    2300
```

FIGURE 23

Name:

Respirator:

Fit Tests

2402

New
2404

Training Sessions

2406

Go Back

Go to Main

Print

Delete Respirator from this Person's Records

[F1] - help. Select fields with tab / shift-tab.
2400

FIGURE 24

―――――――――― Qualitative Fit Test Record (1/2) ――――――――――

Name:
Employee ID/SSN:
Respirator:

Date [mm/dd/yy]:        Size:

Respiratory Hazards Encountered:

Sensitivity Test:                         Results:
 Isoamyl Acetate (Banana Oil)     ( ) Pass ( ) Fail ( ) n/a
 Saccharin: # Squeezes
     ( ) 10  ( ) 20  ( ) 30        ( ) Pass ( ) Fail( ) n/a
 Irritant Smoke                      ( ) Pass ( ) Fail( ) n/a

[ Next Page ]       [ Delete Record ]      [ Done ]  [ Go to Main ]
                                                        [ Print ]

2502 / 2500

[F1] - help. Select fields with tab / shift-tab.

FIGURE 25

Quantitative Fit Test Record (1/2)

Name:
Employee ID/SSN:
Respirator:

Date [mm/dd/yy]:                Size:

Respiratory Hazards Encountered:

Results     Pass/Fail Criteria
            ( ) 10  ( ) 50  ( ) 100  ( ) 250  ( ) 500  ( ) 1000  ( ) 1250
Fit Factor          ← 2602
Trial 1:
Trial 2:
Trial 3:
Lowest:

[Next Page]        [Delete Record]        [Done]

[F1] - help. Select fields with tab / shift-tab.
          ↑
        2600

[Print]     [Go to Main]

FIGURE 26

═══ Respirator Training and Protocol ═══

RESPIRATOR TRAINING AND PROTOCOL

The following procedure will be followed for the training of employees required to use respiratory protection.

STEP 1. INSTRUCTION ON HEALTH EFFECTS OF RESPIRATORY HAZARDS _2902_

STEP 2. INSTRUCTION OF USES AND LIMITATIONS

All respirators have use limitations. There is not one all-purpose respirator. The respirators on which you will be trained were selected by the company for your work environment. The uses and limitations of the respirator on the NIOSH approval label and other information contained on/in each respirator package will be covered.

[ Go to Related Item ] —2904

[ Print ] —2906

[ Go Back ]

[ Go to Main ]

[F1] - help. Select fields with tab / shift-tab.

===== Respirator Training and Protocol =====

RESPIRATOR TRAINING AND PROTOCOL

The following procedure will be followed for the training of employees required to use respiratory protection.

STEP 1. INSTRUCTION ON HEALTH EFFECTS OF RESPIRATORY HAZARDS

——————————————— Go to ... ———————————————

The material sa | Training (requirements)                          | place provide
information on  | Training Program Attendance Roster (form)        | ials. A list
of potential co | Training Sessions (records)                      | ty data
sheets are avai |                                                  |
                | Cancel                                           |

STEP 2. INSTRUC

All respirators                                                     urpose

[ Go to Related Item ]                          [ Print ]    [ Go Back ]    [ Go to Main ]

[F1] - help.  Select fields with tab / shift-tab.

```
┌─────────────────────────────────────────────────────────────┐
│  ─── Items Likely to be Requested by an Auditor ───         │
│  Select the Items of Interest, then View or Print           │
│                                                             │
│          [ ] Program Requirements                           │
│                                                             │
│  Procedures and Records:                                    │
│                                                             │
│  Medical Evaluation  [ ] Most Recent Request for Medical Clearance Records │
│                                                             │
│         Training  [ ] Training Protocol                     │
│                   [ ] Most Recent Attendance Rosters        │
│                                                             │
│      Fit Testing  [ ] Qualitative Fit Test Protocol         │
│                   [ ] Most Recent Fit Test Records          │
│                                                             │
│  Breathing Air Quality [ ] Most Recent Breathing Air Quality Records │
│                                                             │
│  Program Evaluation [ ] Most Recent Program Evaluation Record │
│                                                             │
│           ┌──────┐    ┌───────┐        ┌────────────┐       │
│           │ View │    │ Print │        │ Go to Main │       │
│           └──────┘    └───────┘        └────────────┘       │
│                                                             │
│  [F1] - help. Select fields with tab / shift-tab.           │
└─────────────────────────────────────────────────────────────┘
           ↑
         3300
```

FIGURE 33

```
                    Select a Training Session
Date      Company Model  Type

04/11/94
04/11/94
```

Search field:
*DATE
Search for:

Single Selection

Use Tab, Arrow Keys, or Mouse to Scroll to Right for more respirator Info

| Accept | F2 | Cancel | Esc |
| Search | F5 | Again | Alt-F5 |

SYSTEM AND METHOD FOR DEVELOPING AND/OR MAINTAINING A WORKPLACE RESPIRATORY PROTECTION PROGRAM

This is a Continuation of U.S. application Ser. No. 08/233,589, filed Apr. 26, 1994, now abandoned.

TECHNICAL FIELD

The present invention relates to a system and method for developing and/or maintaining a workplace respiratory protection program.

BACKGROUND OF THE INVENTION

Government regulatory bodies, such as the Occupational Safety and Health Administration (OSHA) in the United States of America, and standards setting organizations, such as the Canadian Standards Administration (CSA) in Canada, promulgate regulations and establish standards intended to control the safety of the workplaces provided by employers to their employees. For example, one such regulation promulgated by OSHA requires employers to establish respiratory protection programs. This regulation is intended to reduce exposure to employees against such airborne contaminants as occupational dusts, fumes, mists, radionuclides, gases, and vapors. Where feasible, effective engineering controls are to be implemented in order to maintain such airborne contaminants at levels which are considered to be non-hazardous to employees. However, where effective engineering controls are not feasible, or while such engineering controls are being designed, implemented, and evaluated, use of respirators may be required in order to protect employees from exposure to these airborne contaminants.

In the past, there have been numerous problems connected with workplace respiratory protection programs. The development of such workplace respiratory protection programs has involved haphazard and non-structured searches for the various governmental regulations and standards which impact respiratory protection in a workplace and for the respirators and standard operating procedures which must be adopted to assure compliance with the applicable governmental regulations and standards. The development of the workplace respiratory protection program to ensure compliance with the applicable governmental regulations and standards usually also requires the accumulation and maintenance of a great many forms. These forms may include, for example, medical questionnaires, requests for medical clearance, fit test results, exposure assessments, various evaluation forms, and the like. Once the workplace respiratory protection program has been developed, this program must be maintained in order to assure continuing compliance with the applicable governmental regulations and standards.

Moreover, responsibility within the workplace for the development and maintenance of the workplace respiratory protection program may be delegated to a great many people, may be decentralized, and may not be clearly defined. The forms created during both the development and the maintenance of the workplace respiratory protection program typically are filled out by a great many people and are stored in a great many locations within a workplace, which can make finding these records difficult. The documentation, which relates to the respirators and which are approved for each employee, for each type of job within the workplace, for each workplace location, and for each type of contaminant to which employees may be exposed, may also be scattered throughout a workplace. Standard operating procedures, such as those relating to cleaning, inspection, and training, may not be easily accessible. Training requirements and procedures with respect to the use and maintenance of respirators may not be consistently and centrally controlled within a workplace.

Furthermore, workplaces are frequently audited to assure that the employer is in compliance with the applicable governmental regulations and standards. Because the forms and records used in the workplace respiratory protection program are typically decentralized and may be scattered throughout a workplace, it may be extremely difficult for the employer to prepare for an audit. Failure to assure the auditor that the employer is in compliance with governmental regulations and standards can lead to the imposition of fines and other penalties.

While some efforts have been made in the past in an attempt to manage compliance with various governmental regulations and standards relating to health and safety, such efforts have not been adequate and have not involved complete workplace respiratory protection programs. Thus, software application programs exist which allow the users thereof to create and maintain databases containing certain employee records relating to health and safety. These records may include medical tests, physical examinations, accident and illness reports, and the treatments prescribed as a result of the reported accidents and illnesses. These records allow accidents and illnesses to be tracked and, hopefully, managed. Some software application programs assist the user in filling out the forms required by government regulators for the reporting of employee accidents and illnesses. Some software application programs assist the user in maintaining records relating to hygiene and to workplace safety training.

It has even been known to integrate one or more of these software application programs with each other and with software application programs which allow maintenance of Material Safety Data Sheets and records related to hazardous materials. There are also software application programs which allow employers to monitor and track employee demographics, injuries and illnesses, worker's compensation claims, the workplace environment, employee medical health, and hazardous materials in the workplace.

However, such software application programs have substantial problems. For example, none of these software application programs relate to respiratory protection, and none of these software application programs fully integrate the development and maintenance of a workplace respiratory protection program for the protection of employees in the workplace. Accordingly, none of these software application programs integrate all aspects of workplace respiratory protection programs such as (i) the forms which are useful in developing and maintaining a workplace respiratory protection program, (ii) the training of employees which is necessary to ensure that the workplace respiratory protection program is effective, (iii) the database which is necessary to provide all of the information required during the development and maintenance of a workplace respiratory protection program, (iv) the customization which is necessary to permit the employer to tailor a workplace respiratory protection program to the employer's workplace, (v) the ability of the employer and employees to read the information provided by a fully informative workplace respiratory protection program, and (vi) the assistance helpful to the employer in preparing for an audit of the workplace respiratory protection program. The present invention solves one or more of the above described problems.

SUMMARY OF THE INVENTION

In one aspect of the present invention, a method of developing a workplace respiratory protection program comprises the steps, performed by a data processing system, of (a) executing program code to retrieve requirements of the workplace respiratory protection program from a database of the data processing system and to display the requirements of the workplace respiratory protection program to a user, and (b) executing program code to prompt development of the workplace respiratory protection program based upon the requirements of the workplace respiratory protection program stored in the database and displayed to the user.

In another aspect of the present invention, a method of developing a workplace respiratory protection program comprises the steps, performed by a data processing system, of (a) executing first program code to display requirements for a workplace respiratory protection program, (b) executing second program code in order to display forms useful in the development of the workplace respiratory protection program, and (c) linking the first and second program codes in hypertext fashion.

In still another aspect of the present invention, a method of developing a workplace respiratory protection program comprises the steps, performed by a data processing system, of (a) executing first program code to retrieve requirements of the workplace respiratory protection program from a database of the data processing system and to display the requirements of the workplace respiratory protection program to a user, and (b) executing second program code to prompt the development of the workplace respiratory protection program which is based upon the requirements of the workplace respiratory protection program and which complies with governmental respiratory protection regulations of first and/or second countries.

In yet another aspect of the present invention, a method of customizing a workplace respiratory protection program comprises the steps, performed by a data processing system, of (a) executing first program code to prompt customization of workplace respiratory protection requirements of the workplace respiratory protection program, and (b) executing second program code in order to display forms useful in the customization of the workplace respiratory protection program.

In a still further aspect of the present invention, a method of developing a workplace respiratory protection program and of preparing for an audit thereof comprises the steps, performed by a data processing system, of (a) executing first program code to prompt the development of a workplace respiratory protection program which complies with governmental respiratory protection regulations, and (b) executing second program code in order to assist a user in preparing for an audit of the workplace respiratory protection program.

In yet a still further aspect of the present invention, a method of developing and maintaining a workplace respiratory protection program comprises the steps, performed by a data processing system, of (a) executing first program code to prompt the development of a workplace respiratory protection program which includes respiratory protection requirements and creation of records, and (b) executing second program code in order to maintain the workplace respiratory protection program and in order to maintain the records so as to stay in compliance with the respiratory protection requirements.

In yet another aspect of the present invention, a method of maintaining a workplace respiratory protection program comprises the steps, performed by a data processing system, of (a) executing program code to prompt maintenance of the workplace respiratory protection program so as to stay in compliance with regulations relating to governmental respiratory protection requirements, and (b) executing program code in response to step (a) in order to display forms useful in the maintenance of the workplace respiratory protection program, wherein the forms are stored in a database of the data processing system.

In still another aspect of the present invention, a method of maintaining a workplace respiratory protection program and of preparing for an audit thereof comprises the steps, performed by a data processing system, of (a) executing first program code to maintain records relating to the workplace respiratory protection program, and (b) executing second program code in order to assist a user in preparing for an audit of the workplace respiratory program.

In yet a still further aspect of the present invention, a method of maintaining a workplace respiratory protection program comprises the steps, performed by a data processing system, of (a) executing program code to maintain records concerning the workplace respiratory protection program to enable an employer to stay in compliance with respiratory protection requirements, and (b) executing program code to display a linking screen containing a personal ID of an employee.

In yet another aspect of the present invention, a method of maintaining a workplace respiratory protection program comprises the steps, performed by a data processing system, of (a) executing program code in order to maintain records for the workplace respiratory protection program, and (b) executing program code to access the records through links, wherein the records are linked to a respirator, and wherein there are records which are accessible through the links.

BRIEF DESCRIPTION OF THE DRAWING

These and other features and advantages will become more apparent from a detailed consideration of the invention when taken in conjunction with the drawing in which:

FIG. 3 is a representation of a screen display which is accessed from the welcome screen of FIG. 2;

FIG. 4 is a representation of a screen display which is accessed from the screen display of FIG. 3 during development of a workplace respiratory protection program;

FIG. 7 is a representation of a screen display which is accessed from the screen display of FIG. 6;

FIG. 10 is a representation of a screen display which is accessed from the screen display of FIG. 9;

FIG. 12 is a representation of a screen display which is accessed from the screen display of FIG. 11;

FIG. 13 is a representation of a screen display which is accessed from the screen display of FIG. 5;

FIG. 14 is a representation of a screen display which is accessed from the screen display of FIG. 13;

FIG. 15 is a representation of a screen display which is accessed from the screen display of FIG. 14;

FIG. 16 is a representation of a screen display which is accessed from the screen display of FIG. 5;

FIG. 22 is a representation of a screen display which is accessed from the screen display of FIG. 14;

FIG. 23 is a representation of a screen display which is accessed from the screen display of FIG. 14;

FIG. 24 is a representation of a screen display which is accessed from the screen display of FIG. 14;

FIG. 25 is a representation of a screen display which is accessed from the screen display of FIG. 24;

FIG. 26 is a representation of a screen display which is accessed from the screen display of FIG. 24;

FIG. 29 is a representation of a screen display which is accessed from the screen display of FIG. 28;

FIG. 30 is a representation of a screen display which is accessed from the screen display of FIG. 29;

FIG. 33 is a representation of a screen display which is accessed from the screen display of FIG. 17;

DETAILED DESCRIPTION OF THE INVENTION

Figure 1:
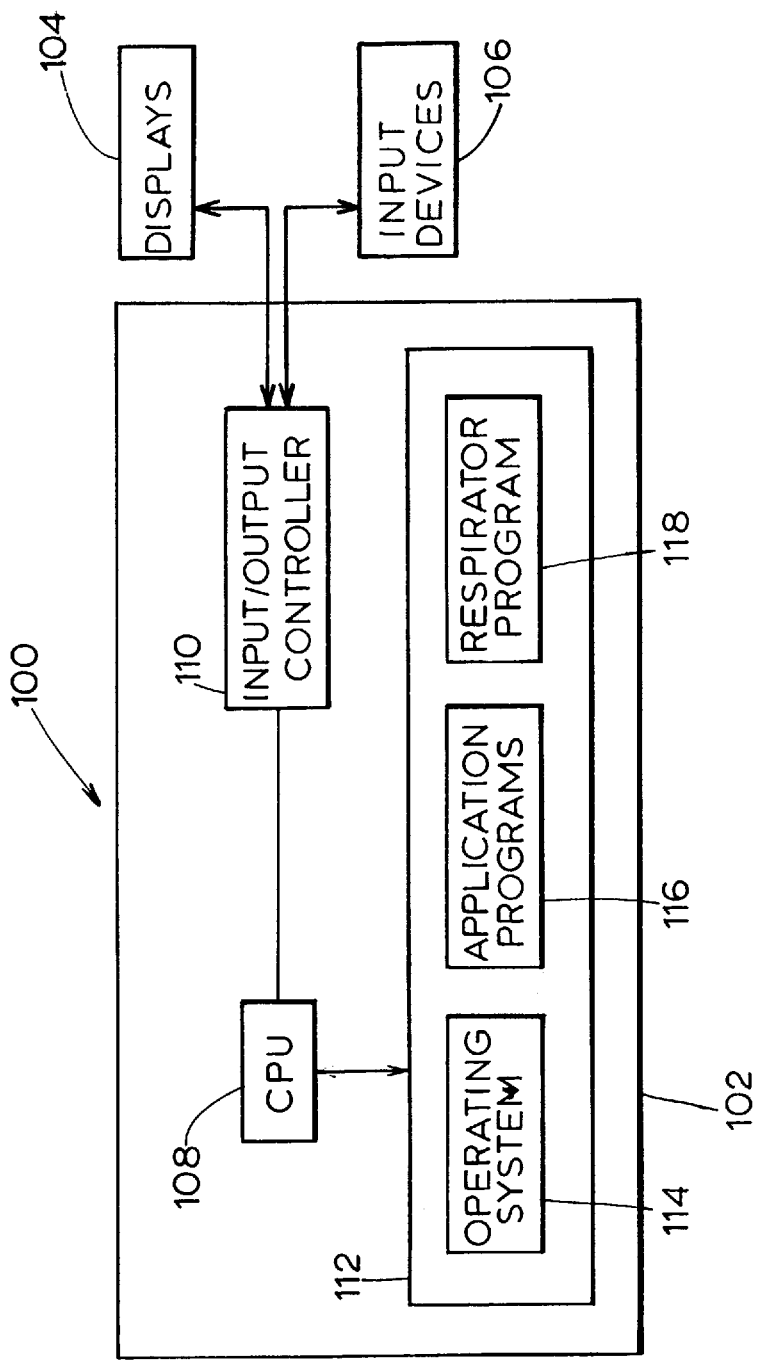
FIG. 1 is a block diagram of a data processing system which can be configured in accordance with the present invention.

One possible operating environment of the present invention is a data processing system, such as a data processing system 100 shown in FIG. 1. However, it should be noted that the present invention can be used in any other operating environment. The data processing system 100, for example, can be a personal computer, or a work station, and can include a processor 102, one or more display terminals 104, and one or more input devices 106. The display terminals 104 may include, for example, a monitor having a viewing screen, a printer, and/or the like. The input devices 106 may include, for example, a mouse, a keyboard, and/or similar devices.

The processor 102 may include a central processing unit (CPU) 108 which communicates with the display terminals 104 and with the input devices 106 through an input/output controller 110, and which processes program code stored in a memory 112. The program code stored in the memory 112 includes, for example, an operating system 114, various application programs 116, and a respirator program 118. The application programs 116 may include word processing programs, spreadsheet programs, and the like. The respirator program 118 is executed by the processor 102 in order to perform the functions of the present invention.

Figure 2:
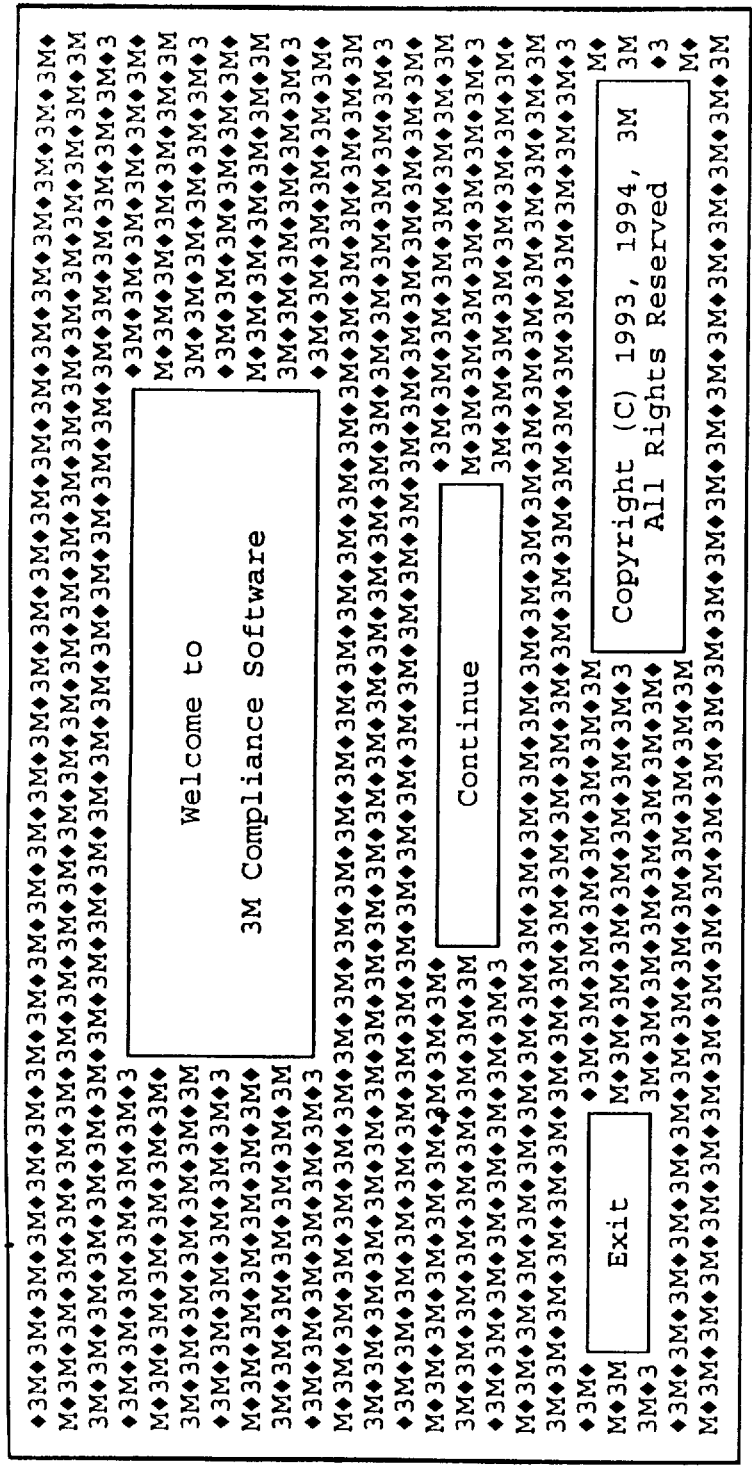
FIG. 2 is a representation of a welcome screen which is presented to a user of the present invention.

When the respirator program 118 is first entered, a user is presented with a welcome screen 200 such as that shown in FIG. 2. As shown in FIG. 2, the user can either continue to execute the respirator program 118, or the user can exit therefrom.

If the user elects to continue execution of the respirator program 118, the user is presented with a screen display 300 as shown in FIG. 3. This screen display asks the user to confirm both the current date and whether the user wishes to have help in getting started with the development of a workplace respiratory protection program. Ordinarily, a user who wishes to begin the development of a workplace respiratory protection program will request help in getting started.

By entering a Y in a region 302 of the screen display 300, the user indicates a desire for help in getting started with the development of a workplace respiratory protection program. If the user selects the development mode of the present invention by entering a Y in the region 302 of the screen display 300, a screen display 400 as shown in FIG. 4 is presented to the user. The screen display 400 presents introductory information about starting the development of a workplace respiratory protection program. As shown in FIG. 4, the screen display 400 may inform the user that, after completion of the items on a Getting Started screen display, any items contained in the workplace respiratory protection program may be viewed or modified from a Main Menu screen display which will be described hereinafter.

Figure 5:
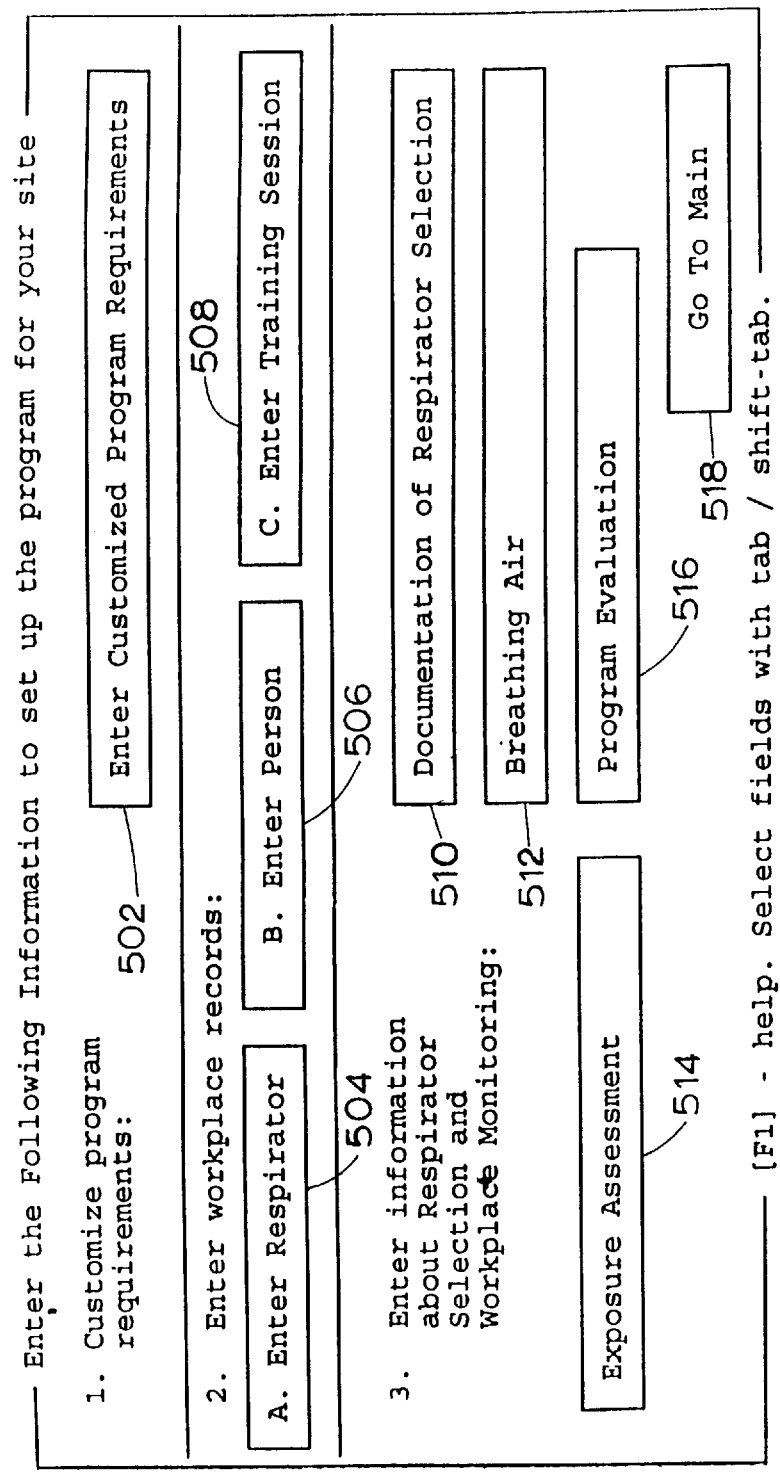
FIG. 5 is a representation of a screen display which is accessed from the screen display of FIG. 4.

When the user indicates on the screen display 400 that it is OK to proceed with the development of a workplace respiratory protection program, the respirator program 118 causes a screen display 500 as shown in FIG. 5 to be presented to the user. The screen display 500 includes a plurality of buttons 502–518 which are selectable by the user. Selection of the button 518 returns the user to the Main Menu of the respirator program 118. Buttons may be selected by using arrow keys, the tab key, and/or the like, in order to position a cursor over a button and by then pressing the enter key. Alternatively, a mouse may be clicked on a button. Other ways of selecting buttons are, of course, possible.

Selection of the butt on 502 allows the user to customize the program requirements of the workplace respiratory protection program to be developed. Selection of the buttons 504, 506, and 508 permit the user to create workplace records concerning the workplace respiratory protection program. Specifically, selection of the button 504 permits the user to enter into these records information concerning the respirators which might be used in the workplace respiratory protection program, selection of the button 506 allows the user to enter into these records information concerning employees, and selection of the button 508 permits the user to enter into these records information concerning employee training sessions.

Selection of the buttons 510, 512, 514, and 516 permit the user to enter information about the selection of respirators, about contaminant exposure in the workplace, about the monitoring of the workplace environment, and about evaluation of the workplace respiratory protection program. Specifically, selection of the button 510 permits the user to enter information concerning the selection of respirators. For example, such information may be entered by the job and/or location in which a respirator is to be used. Selection of the button 512 permits the user to enter information concerning the contaminants which may affect the breathability of the air in the workplace. Selection of the button 514 allows the user to enter information concerning the user's assessment of the exposure of employees to the contaminants which may be found at locations or during jobs within the workplace. Selection of the button 516 permits the user to enter information concerning the evaluation of the workplace respiratory protection program.

Figure 6:
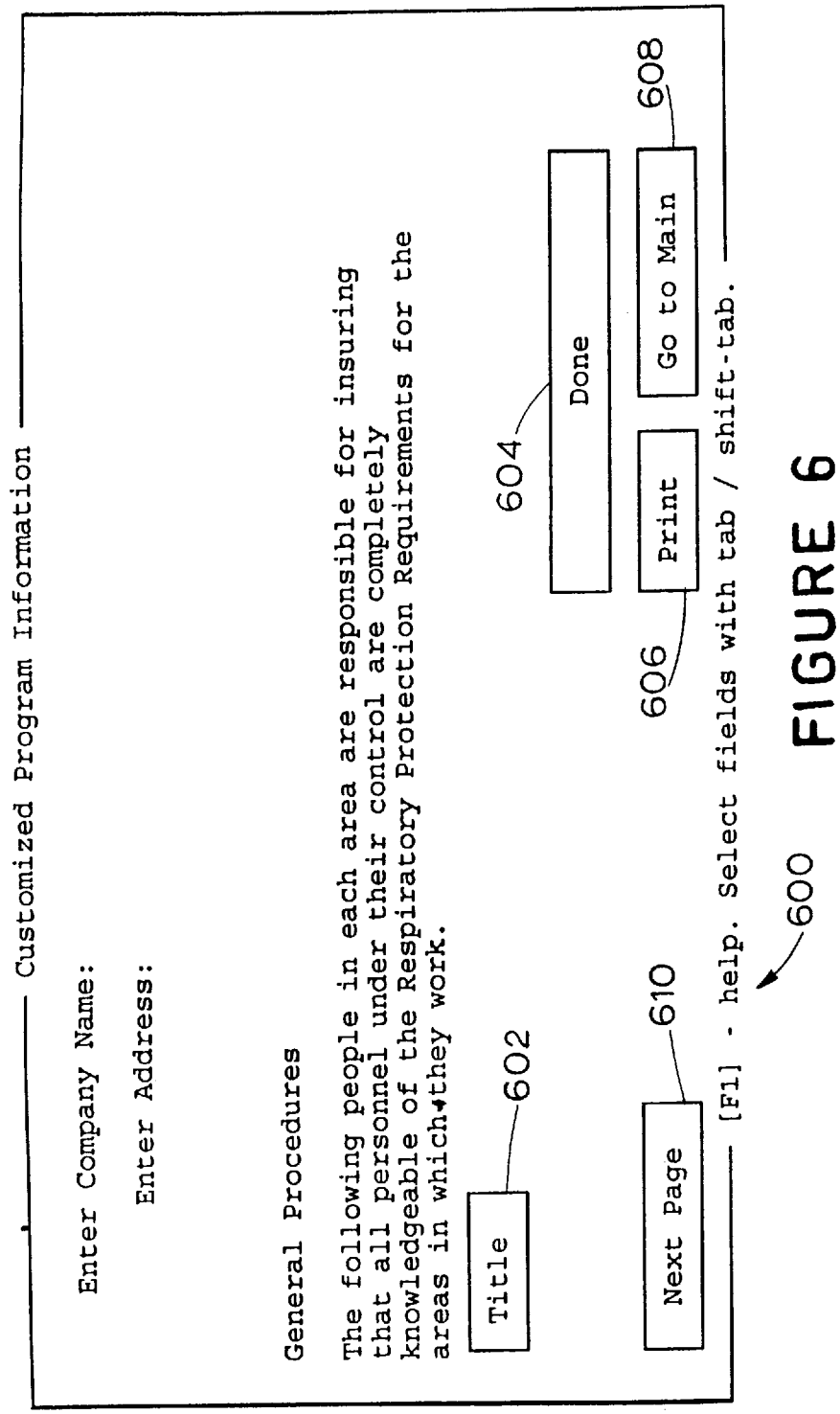
FIG. 6 is a representation of a screen display which is accessed from the screen display of FIG. 5.

Selection of the button 502 permits the user to customize the requirements of the workplace respiratory protection program. When the button 502 is selected by the user, the user is presented with a screen display 600 as shown in FIG. 6 to begin the process of customization. Within this screen display 600, the user may enter the name and address of the company (i.e., employer) for which the workplace respiratory protection program is being developed. The user may enter, in the region next to a button 602, the title of the people in each area who are responsible for ensuring that all personnel under their control are completely knowledgeable with the workplace respiratory protection program requirements for the areas in which they work. Selection of the button 602 presents the user with a list of possible titles. The user may select a title from this list or may insert any other title.

Selection of a button 604 in the screen display 600 permits the user to indicate that customization of the workplace respiratory protection program has been completed. If the button 604 is selected, the respirator program 118 returns the user to the screen display 500. Selection of a button 606 allows the user to print the current screen display 600, to print a group of screen displays, or to print all of the customization screen displays involved in the customization of the workplace respiratory protection program. A button 608 allows the user to return to the Main Menu. A button 610 allows the user to proceed to the next page for the customization of further program requirements of the workplace respiratory protection program.

After the appropriate information is entered into the screen display 600 by the user, customization may be continued by the user by selection of the button 610 which causes a screen display 700 as shown in FIG. 7 to be displayed. This screen display 700 allows the user to select the country for which the workplace respiratory protection program is being developed. Thus, as indicated by the screen display 700, the respirator program 118 contains the necessary knowledge to help a user in the development of workplace respiratory protection programs which will satisfy the governmental regulations and standards of more than one country. In the specific example shown by the screen display 700 of FIG. 7, the respirator program 118 is configured to permit the development of workplace respiratory protection programs to satisfy the governmental regulations and standards of the United States of America and of Canada. Thus, if the U.S. is selected, the respirator program 118 displays knowledge to the user tailored to U.S. requirements; and, if Canada is selected, the respirator program 118 displays knowledge to the user tailored to Canadian standards.

Also, as shown by the screen display 700, the user may indicate the types of respirators which are used in the employer's workplace, may print those items which may be printed by selection of the print button 606 of the screen display 600, may terminate customization (by selecting the Done button), may return to the Main Menu, may return to the previous page, and may proceed to the next page.

Although the next pages which may be accessed through execution of the respirator program 118 are not specifically shown herein, these next pages may include any of the following: (i) a page permitting the user to provide the names, titles, and departments of a person having overall responsibility for the administration of the workplace respiratory protection program and of a person having responsibility for identifying and measuring contaminants in the workplace; (ii) a page permitting the user to provide the names, titles, and departments of a person having responsibility for evaluating the health of employees and of a person having responsibility for directing and coordinating engineering projects related to the workplace respiratory protection program; (iii) a page permitting the user to provide the name, title, and department of a person having responsibility for the selection, issuance, training, and/or fit testing of all respirators which may be used in the workplace respiratory protection program and to designate the effective date of the workplace respiratory protection program; (iv) a page permitting the user to select the periodicity within which employees must be medically evaluated and to include exceptions within a scrollable window; (v) a page permitting the user to designate where copies of medical clearance request records are maintained; (vi) a page permitting the user to designate the periodicity for making exposure assessments and to indicate where records of such exposure assessments are maintained; (vii) a page permitting the user to designate the criteria being employed to govern the selection of respirator types; (viii) a page permitting the user to designate in a scrollable window those from whom respirators may be purchased and to list in a scrollable window the approved respirators which may be used in the workplace respiratory protection program; (ix) a page permitting the user to designate a respirator instructor and to indicate where records concerning the training of employees are maintained; (x) a page permitting the user to designate where fit testing records are maintained; (xi) a page permitting the user to designate those employees who are responsible for spot checking respirators for fit, usage, and condition and to designate a person to whom defective respirators are to be returned; and, (xii) a page designating the periodicity for evaluating the workplace respiratory protection program and where copies of program summary reports may be found.

As in the case of the screen displays 600 and 700, the screen displays containing these pages may have buttons allowing the user to print those items which may be printed by selection of the print button 606 of the screen display 600, to terminate customization (indicating that customization is done), to return to the Main Menu, to return to the previous page, and to proceed to the next page. It should be apparent that more or fewer pages may be provided than those described above. Selection of the Done button on any of these screen displays to indicate that the customization process is completed returns the user to the screen display 500.

After these requirements of the workplace respiratory protection program have been customized, the user may continue the development of the workplace respiratory protection program by selecting the button 504 from the screen display 500. Where the performance of jobs by employees in locations of a workplace expose the employees to hazardous airborne contaminants, the employees are required to use respirators. Selection of the button 504 permits the user to designate respirators by location and by job within the workplace.

Figure 8:
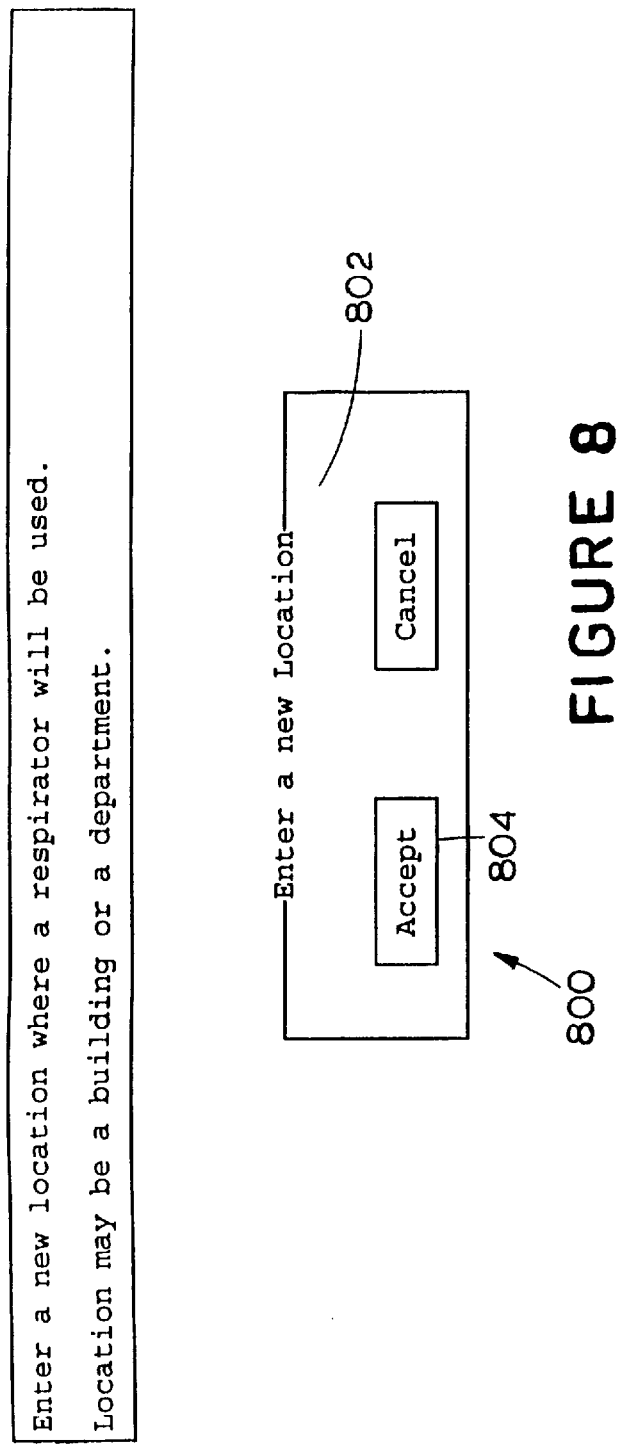
FIG. 8 is a screen display which is accessed from the screen display of FIG. 5.
Figure 9:
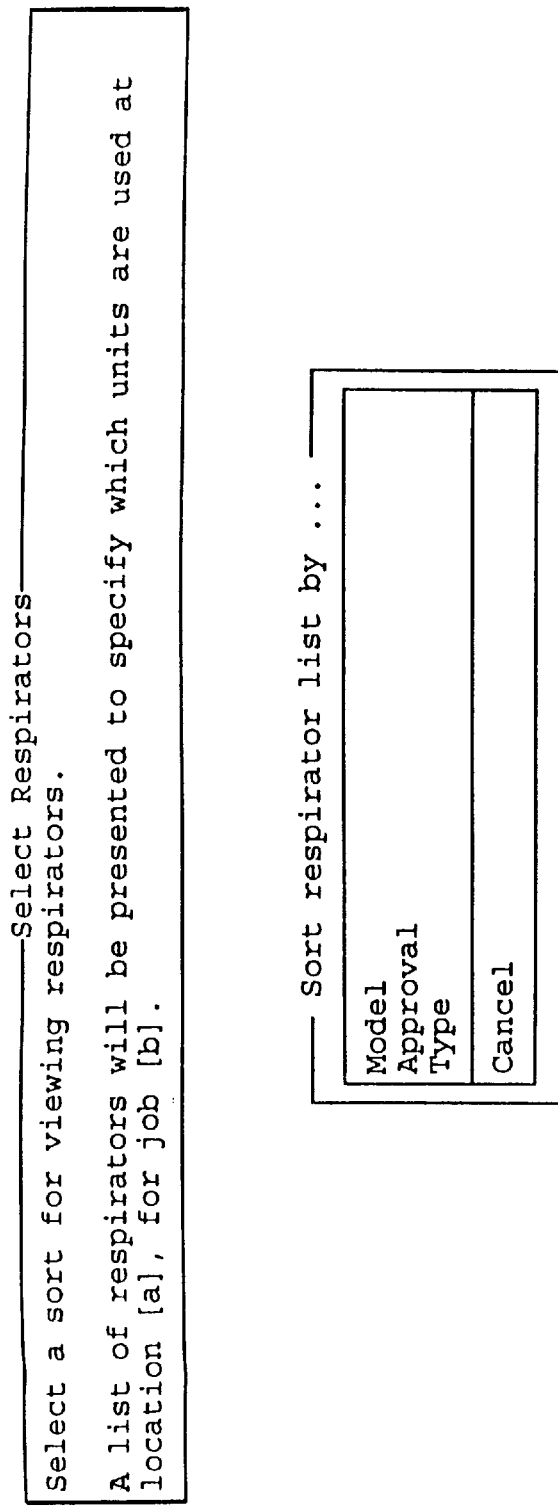
FIG. 9 is a representation of a screen display which is accessed from the screen display of FIG. 8.

Accordingly, the first time that a user selects the button 504, a screen display 800 as shown in FIG. 8 is presented to the user. The screen display 800 allows the user to enter a location of the workplace where the use of a respirator is required. Assuming that the user enters a location for a respirator in a region 802 of the screen display 800 and indicates correct entry by selecting a button 804, the user is then presented with a screen display similar to the screen display 800 but in which the user is requested to enter the title of the job for which the respirator is to be used. The user is then presented with a screen display 900 as shown in FIG. 9 which allows the user to view respirators as sorted by respirator model, by respirator approval, or by respirator type.

For example, if the user requests that the respirators be sorted by type, the user is presented with a screen display 1000 as shown in FIG. 10. The user may select a respirator from the list of respirators presented in the screen display 1000 by highlighting the desired respirator, by pressing the enter key to select the highlighted respirator (which places a check mark in the check column), and by pressing the F2 function key. The respirator program 118 may be provided with a list of pre-approved respirators. Respirators may be added to this list by pressing the insert key. Selecting a respirator returns the user to the screen display 500. This process of specifying a location, a job, and a respirator thereby associates the specified location and the specified job with the specified respirator. Thus, a respirator may be selected for an employee according to the job to be performed by the employee and to the location at which the job is to be performed by the employee.

Figure 11:
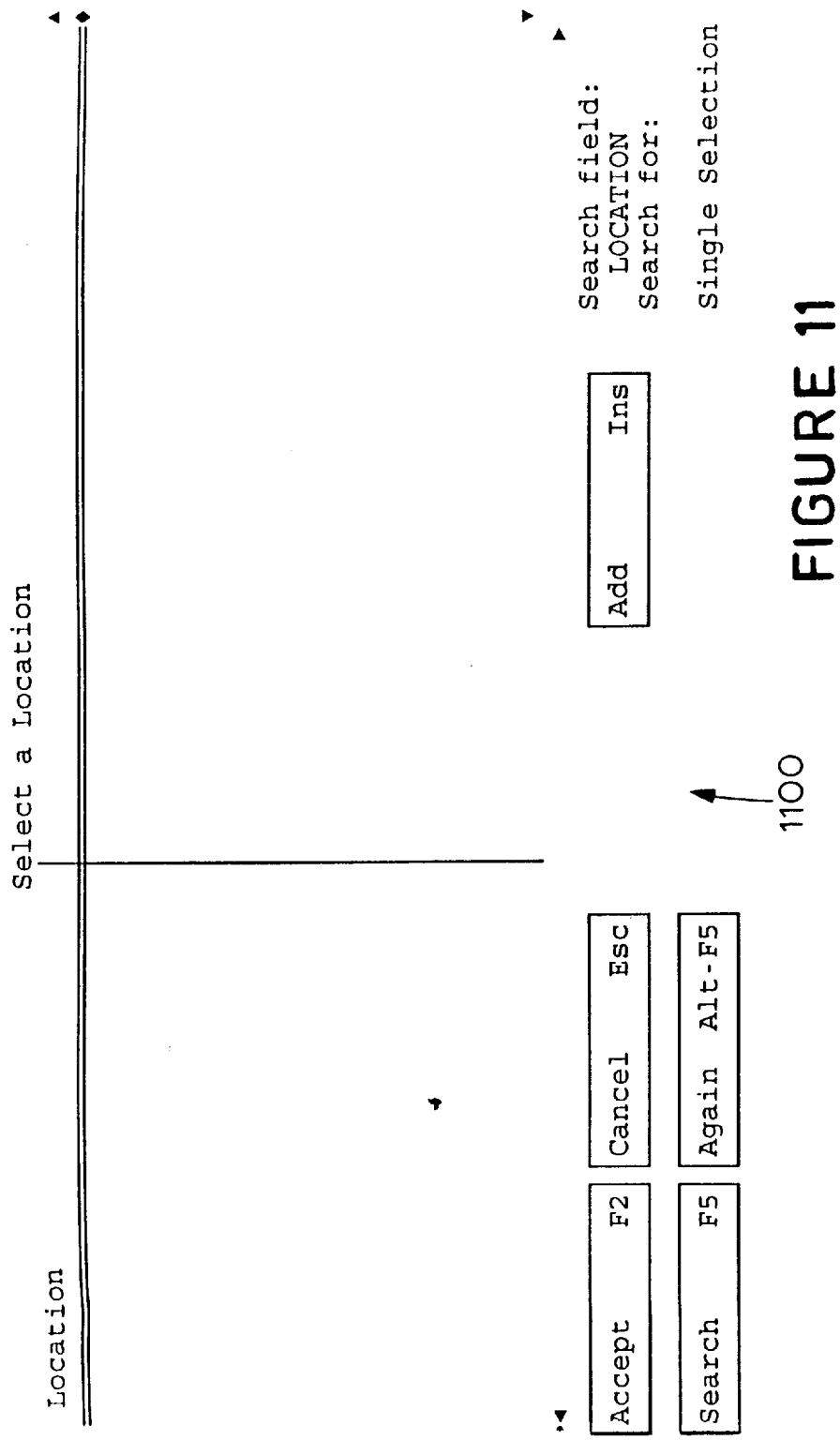
FIG. 11 is a representation of a screen display which is accessed from the screen display of FIG. 5.

Upon return to the display 500, selection of the button 504 presents the user with a screen display 1100 shown in FIG. 11. The screen display 1100 lists the locations previously designated. A second location can be added by pressing the insert key which presents the screen display 800 to the user. A second location can then be specified in the region 802. If this second location is accepted, the user is presented with a screen display 1200 shown in FIG. 12. The screen display 1200 lists the jobs previously designated. A second job can be added by pressing the insert key which presents a screen display similar to the screen display 800 to the user but in which the user may enter a job in a region similar to the region 802. A second job can then be specified. If this second job is accepted, the user is presented with the screen display 900 shown in FIG. 9 from which the user can specify a respirator, as before. The user is then returned to the screen display 500 from which additional locations, jobs, and respirators can be specified.

Figure 14:
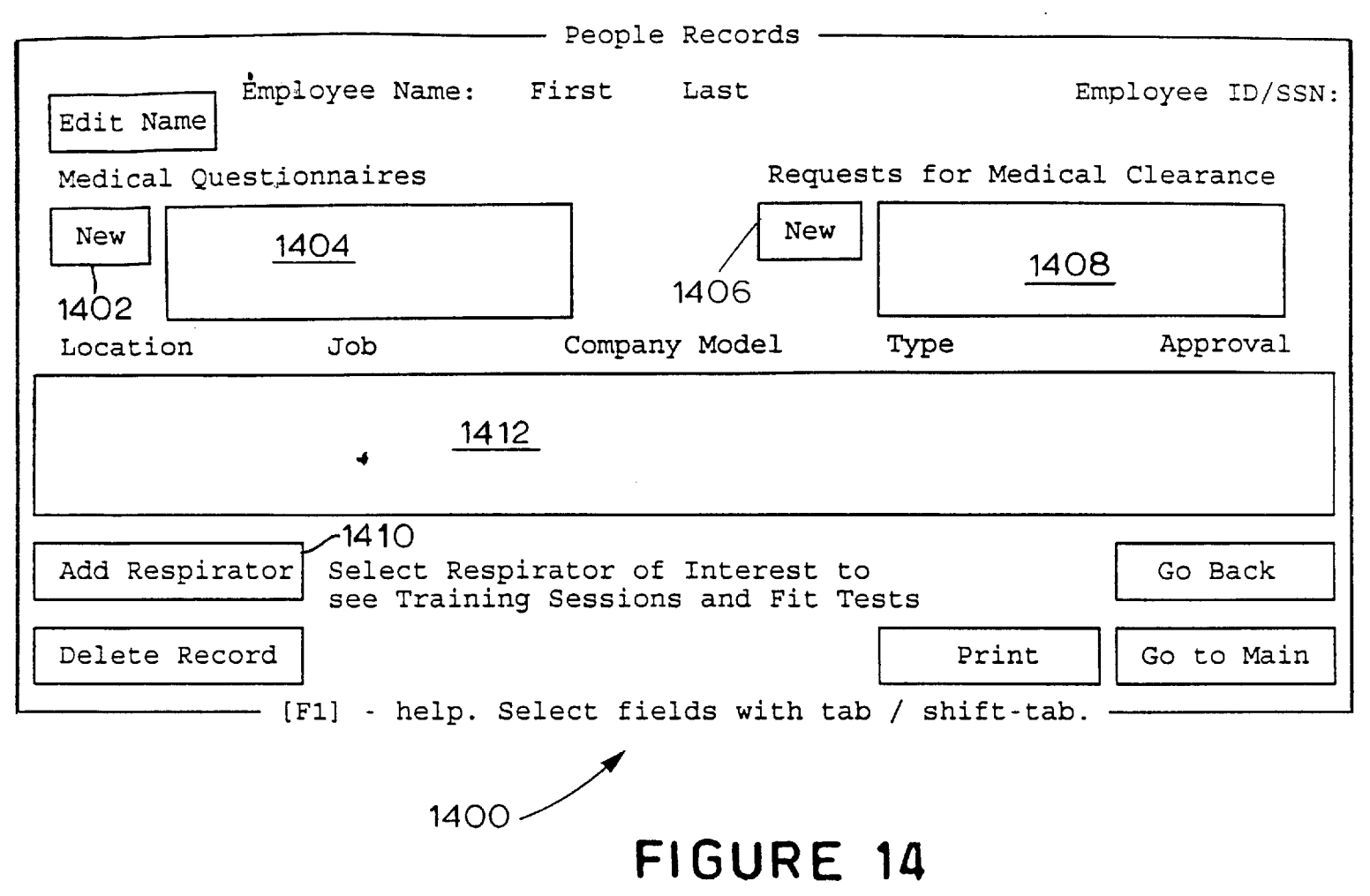

Selection of the button 506 of the screen display 500 presents the user with a screen display 1300 as shown in FIG. 13. In the screen display 1300, the user may designate, in a region 1302, the last name of an employee who is to use a respirator, and may indicate acceptance of the employee designation by selection of an Accept button 1304. This screen display may, if desired, be followed by similar screen displays in which the first name and an employee I.D. number are designated for the employee. When this information has been entered, and accepted, a screen display 1400, as shown in FIG. 14, is presented to the user to permit the user to create a record concerning the designated employee. As shown, the screen display 1400 includes the name and employee identification for the designated employee, and allows the name of the employee to be edited.

This record provides a link between each employee and various records concerning that employee. Accordingly, this record permits access to other employee records in a hypertext function. For example, through the screen display 1400, medical questionnaires and requests for medical clearance concerning an employee may be linked to an individual employee. Also, specific respirators, their locations, and the jobs for which they are to be used, may also be linked to an employee. Furthermore, training sessions and fit tests with respect to designated respirators may be linked to an employee. Thus, these different portions of the respirator program 118 are linked by a hypertext function. As discussed elsewhere herein, other portions of the respirator program 118 may be linked as well.

During the development of the workplace respiratory protection program, medical questionnaires and requests for medical clearance may be filled out for each employee. Accordingly, by selecting a button 1402 of the screen display 1400, the user is asked to enter the date for a medical questionnaire and then a medical questionnaire form is presented to the user which can be completed by the user concerning the employee indicated by the screen display 1400. After completing the medical questionnaire, the date of the questionnaire is presented to the user in a region 1404 of the screen display 1400. However, medical questionnaires themselves are not stored in the data processing system 100 by the respirator program 118, and may not be accessed by use of the respirator program 118 for privacy reasons.

By selecting a button 1406 of the screen display 1400, the user is asked to enter the date for a request for medical clearance, and then a request for medical clearance form is presented to the user which can be completed by the user concerning the employee indicated by the screen display 1400. This form asks the user to indicate the type of respirator which the employee should use, the level of work which the employee is permitted, how often an employee may engage in a particular activity, and the like. After completing the request for medical clearance form, the date of this request is presented to the user in a region 1408 of the screen display 1400. The medical questionnaire and request for medical clearance forms will be discussed in additional detail hereinbelow.

During the development of the workplace respiratory protection program, respirators may be added for the employee indicated by the screen display 1400. Accordingly, by selecting a button 1410, a screen display 1500 as shown in FIG. 15 is presented to the user. The screen display 1500 contains the information created by use of the button 504 from the screen display 500. That is, the screen display 1500 contains a list of respirators specified by location and by job. The user may select a respirator from this list by highlighting the appropriate respirator at the appropriate location and for the appropriate job and by pressing the F2 function key. If so, the chosen respirator is inserted into a region 1412 of the screen display 1400. The information presented in the region 1412 includes the location where the respirator is to be used, the job for which the respirator is to be used, the model designation for the respirator, the type of respirator, and the approval designation for the respirator. Each respirator has a location and a job attached to it. The user selects a unique location-job-respirator combination which then associates a particular respirator for a particular job and location with the identified employee. Multiple respirators may be assigned to a person and presented in the region 1412. A respirator may be removed from a personnel record by selecting a delete button.

In this fashion, an employee may be linked to his medical questionnaires, requests for medical clearance, respirators, and the like. As will be discussed in more detail below, the user may also access training sessions and fit tests for the employee, such as by highlighting a respirator in the region 1412 and by pressing the enter key.

If the user selects the button 508 shown in FIG. 5, the user is first asked to insert a date on which a respirator training program is to be conducted. Then, the user is presented with a screen display 1600 as shown in FIG. 16. The screen display 1600 permits the user to enter a roster of those employees who are to attend the training session. The screen display 1600 includes the name and address of the company, which are inserted automatically from the customized requirements. The user must insert the names of the program administrator and trainer. Selection of a button 1602 presents the user with a list of respirators. If the user selects a respirator from this list, the selected respirator is inserted into a region 1604 of the screen display 1600.

Selection of a button 1606 presents the user with a list of employees. The user may select the employees who are to attend the training session from this list, and the selected employees are inserted into a scrollable region 1608 of the screen display 1600.

Selection of the button 510 of the screen display 500 shown in FIG. 5 presents the user with a screen display, similar to the screen display 1500, from which documentation about respirators may be created by location and/or by job. For example, the information which may be inserted into this documentation by the user may include the following; for each location/job within the workplace, the contaminant against which the respirator is to offer protection; an estimate of the particulate size of the contaminant; information on the contaminant, such as its concentration, hazard ratio, and warning properties; the type of respirator selected for the employee by job and location; the manufacturer of the respirator; and/or the like.

Selection of the button 512 presents the user with a record which the user may fill in concerning any tests of the breathing air quality at a particular location of the workplace.

Selection of the button 514 of the screen display 500 provides a way for the user to create a record concerning the assessment of the exposure of employees. This record may contain, for example, a description of the job category for which a respirator is to be used, the types of contaminants to be guarded against, references to any reports concerning surveys or samples of the contaminants, the concentration of the contaminants, the hazard ratio, and/or the like. This record, therefore, lists the contaminants, and properties of those contaminants, to which an employee may be exposed during performance of a particular job and at a particular location within the workplace.

Selection of the button 516 of the screen display 500 presents the user with a form which may be filled out by the user to create a record of an evaluation of the workplace respiratory protection program. This form may include, for example, a questionnaire to be completed by the user in evaluating the requirements, procedures, controls, training sessions, fit tests, and/or the like of the workplace respiratory protection program. In addition, this form may create a summary of the evaluation.

Figure 17:
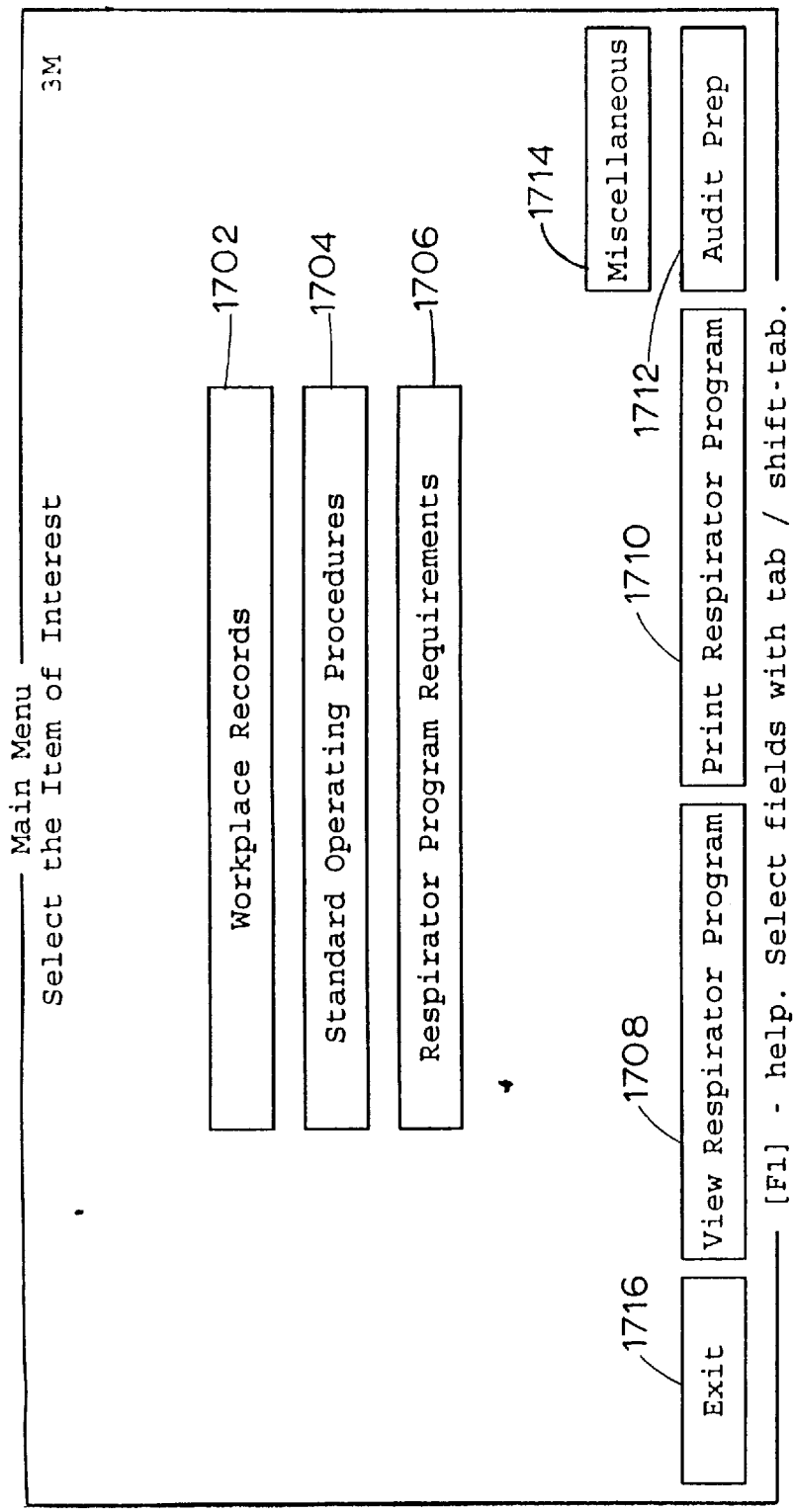
FIG. 17 is a representation of a screen display of a Main Menu which is accessed from the screen displays of either FIG. 3 or FIG. 5.

After development of the workplace respiratory protection program is done, a screen display 1700 shown in FIG. 17 presents the Main Menu of the respirator program 118 to the user. As indicated above, this Main Menu is also presented to the user from the screen display 300 shown in FIG. 3 if the user indicates that the user does not wish help in getting started, i.e. the user has already developed the workplace respiratory protection program. A user may also maintain the workplace respiratory protection program through the Main Menu.

Figure 18:
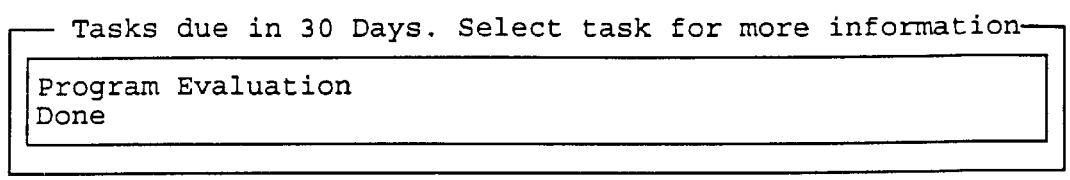
FIG. 18 is a representation of a screen display which is accessed from the screen display of FIG. 3 and which reminds the user of any tasks which are due within a predetermined period of time.

However, before the user is presented with the screen display 1700 from the screen display 300, the user is first presented with an alert screen display in order to alert the user to any tasks which must be completed within a specified period of time, for example, within 30 days of the current date. An example of an alert screen display is the screen display 1800 of FIG. 18 which indicates that the workplace respiratory protection program must be evaluated soon. Accordingly, the respirator program 118 searches its database for any tasks which must be completed within the period of time specified by the alert screen display. If there are tasks to be completed, the user may access more information about each task directly from the alert screen display or select Done to move to the Main Menu 1700. If there are no tasks which are required within the next predetermined period of time, the alert screen display does not appear.

The screen display 1700 includes a button 1702 which, when selected, presents the user with a screen so that the user may find and/or add workplace records. This screen will be discussed below. The screen display 1700 also includes a button 1704 which allows a user to readprint the standard operating procedures involved in the workplace respiratory protection program, a button 1706 which allows the user to read/customize/print the program requirements of the workplace respiratory protection program, a button 1708 which allows the user to view knowledge related to the workplace respiratory protection program in a manual format, a button 1710 which allows the user to print the workplace respiratory protection program, a button 1712 which provides assistance to a user in preparing for an audit such as may be conducted by a government auditor, a button 1714 which presents certain miscellany which may include, for example, printer set up, screen colors, importation of employee names, database maintenance, mouse sensitivity, program configuration, and/or the like.

Figure 19:
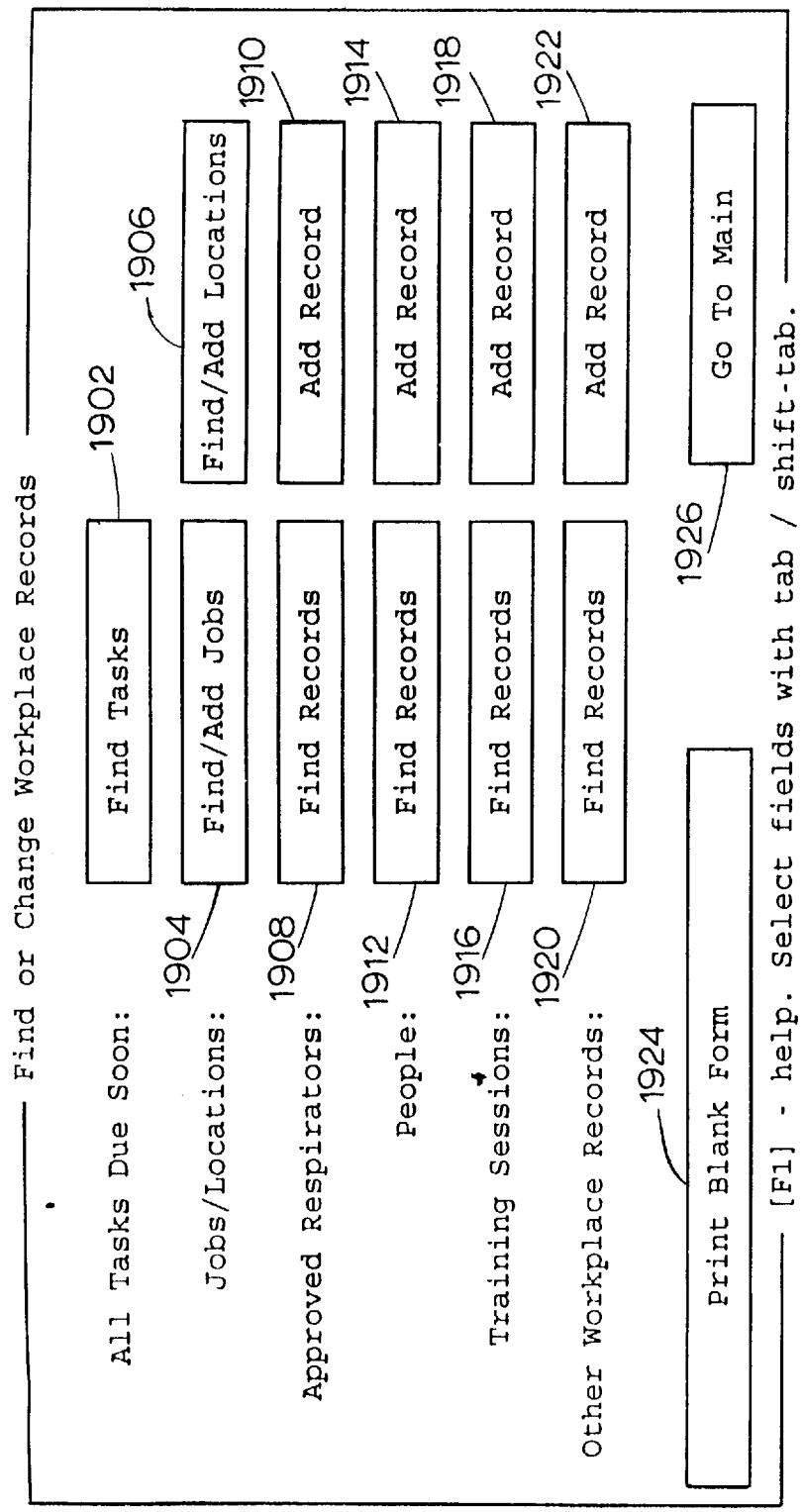
FIG. 19 is a representation of a screen display which is accessed from the screen display of FIG. 17.

Selection of the button 1702 allows the respirator program 118 to find and/or to add workplace records. Accordingly, if the button 1702 of the screen display 1700 shown in FIG. 17 is selected, a screen display 1900 as shown in FIG. 19 is displayed. The screen display 1900 has a button 1902 which allows a user of the data processing system 100 to find those tasks which must be accomplished within a specified amount of time, a button 1904 which allows the user to find/add/delete records related to the jobs for which respirators are required, a button 1906 which allows the user to find/add/delete records related to the locations at which respirators are required, a button 1908 which allows the user to find/delete records related to approved respirators, a button 1910 which allows a user to add records related to approved respirators, a button 1912 which allows the user to find/delete records by employee, a button 1914 which allows the user to add records by employee, a button 1916 which allows a user to find/delete records related to training sessions, a button 1918 which allows a user to add records related to training sessions, a button 1920 which allows a user to find/delete other workplace records, a button 1922 which allows a user to add other workplace records, a button 1924 which allows a user to print blank forms such as medical questionnaires and requests for medical clearance, and a button 1926 which allows the user to jump to the Main Menu presented by the screen display 1700.

Figure 20:
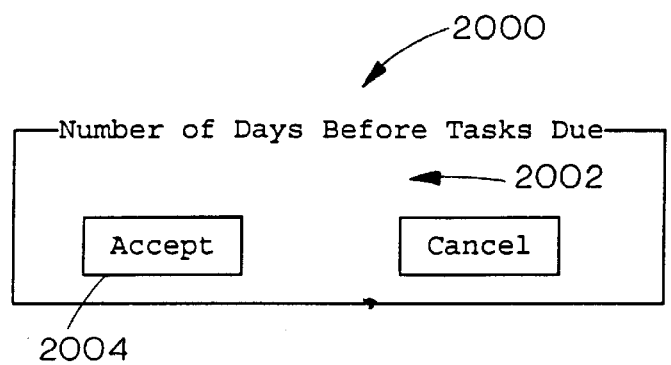
FIG. 20 is a representation of a screen display which is accessed from the screen display of FIG. 19.

When the button 1902 is selected, a screen display 2000 as shown in FIG. 20 is presented to the user to allow the user to specify a search time period within which tasks may be due. By inserting the number of days into a region 2002 of the screen display 2000, the user asks the respirator program 118 to find any tasks due between the current date and the date at the end of the period specified by the number of days entered in the region 2002.

When the number of days (e.g., 30) has been entered in the region 2002 of the screen display 2000 and after this number of days has been accepted by selecting a button 2004, any tasks which are due within the period of time specified by the number of days entered in the region 2002 are displayed to the user. The user can review the tasks which are scheduled to be done within the specified period of time. If no tasks are due within the period of time specified by the user in region 2002 of the screen display 2000, the respirator program 118 returns the user to the screen display 1900.

When the button 1904 is selected from the screen display 1900, the respirator program 118 allows the user to find and/or add records related to the jobs for which respirators are required in much the same way that such records are added during the program development phase (i.e., getting started) described above. Accordingly, the user is presented with a screen display similar to the screen display 1200 in FIG. 12 so that the user can find current jobs by job title or add new job titles to the current list of jobs. Also, each job specified for a respirator may be deleted by selecting a job from the list and selecting the Delete button from a resulting screen.

When the button 1906 is selected from the screen display 1900, the respirator program 118 allows the user to find and/or add records related to the locations at which respirators are required in much the same way that such records are added during the program development phase (i.e., getting started) described above. Accordingly, the user is presented with a screen display similar to the screen display 1100 in FIG. 11 so that the user can find current locations or add new locations to the current list of locations. Also, each location specified for a respirator may be deleted by selecting a location from the list and selecting the Delete button from a resulting screen.

Figure 21:
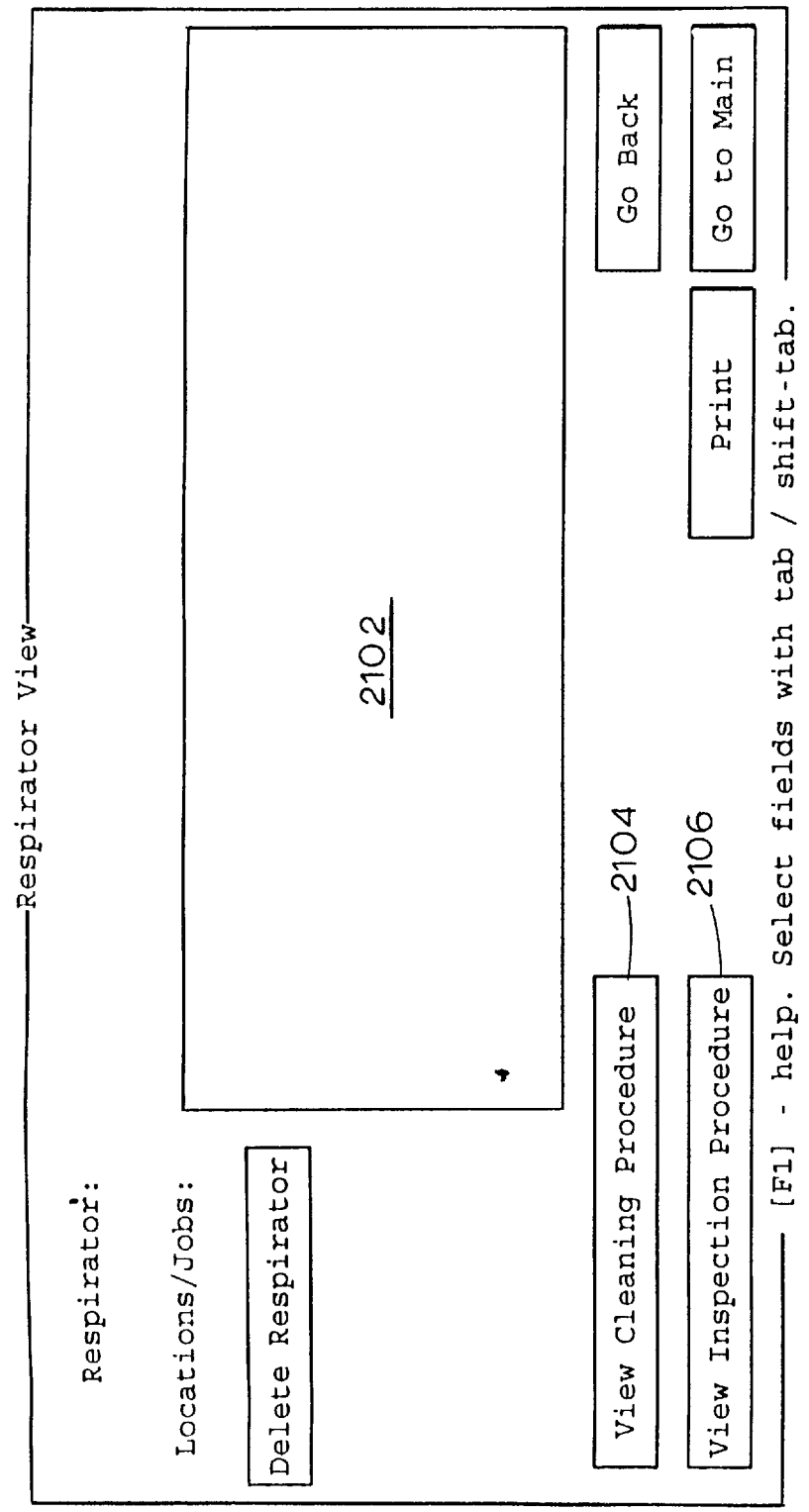
FIG. 21 is a representation of a screen display which is accessed from the screen display of FIG. 19.

The user may search for, and thereby access, a list of approved respirators by selection of the button 1908 of the screen display 1900. Selecting a respirator from this list presents the user with additional information concerning the selected respirator. This information is presented in a screen display 2100 as shown in FIG. 21. The screen display 2100 includes the selected respirator, a scrollable window 2102 containing the locations and jobs for which the selected respirator has been designated, a button 2104 permitting access through a hypertext function to cleaning procedures for the selected respirator, and a button 2106 permitting access through a hypertext function to inspection procedures for the selected respirator. A respirator may be deleted from the list of approved respirators by deleting all jobs and locations for which the respirator is to be used or by selecting a Delete Respirator button. A respirator record may be printed by selecting a Print button. The information displayed by the screen display 2100 is based upon information provided by use of the buttons 504 and/or 1910.

Selecting the button 1910 allows the user to add respirators by location and by job to the list of approved respirators in the same manner that respirators are added by use of the button 504.

When the button 1914 is selected from the screen display 1900, the respirator program 118 allows the user to add employee records in much the same way that such records are added during the program development phase (i.e., getting started) described above. Accordingly, the user is presented with a screen display similar to the screen display 1300 in FIG. 13 so that the user can enter the last name of an employee. The user is also presented with screen displays similar to the screen display 1300 so that the user can enter the first name and employee identification of an employee for whom a record is to be added. Thereafter, a screen display similar to the screen display 1400 shown in FIG. 14 is presented to the user so that the user may enter additional information concerning the employee.

As discussed above, by selecting the button 1402, the user may fill out a medical questionnaire with respect to an identified employee. By selecting the button 1406, the user may fill out a request for medical clearance form for the indicated employee. By selecting the button 1410, the user may select a respirator which is then inserted into the region 1412. In this fashion, an employee may be linked to his medical questionnaires, requests for medical clearance, respirators, and the like. The user may also access training sessions and fit tests for the employee by highlighting a respirator in the region 1412 and by pressing the enter key. In addition, the dates of any existing medical questionnaires are provided in the region 1404, and the dates of any existing requests for medical clearance are provided in the region 1408.

As mentioned above, a medical questionnaire may not be accessed after it has been completed and accepted. It is stored as a hard copy outside of the data processing system 100 for privacy reasons. However, the dates of the records are available in the region 1404 of each person's record. Accordingly, the date of each questionnaire appears in the region 1404 of the screen display 1400. In addition, the date of the most recent questionnaire for each person may be accessed by using the View Respirator Program function of the Main Menu screen display 1700.

An example of a medical questionnaire is shown in FIG. 22 as a screen display 2200. The medical questionnaire allows the user to enter the employee's name, the employee's social security number, the date of the medical questionnaire, the birth date of the employee, the employee's height and weight, an indication as to whether the employee has ever worn a respirator before, and an indication of any apparent difficulties with the use of the respirator (which may be entered in a scrollable window 2202). The company name of the employer is filled in automatically by the respirator program 118 based upon the requirements customized during program development. By accessing additional pages of the medical questionnaire through the use of buttons similar to a button 2204, the user is requested to indicate whether the employee has had any of the illnesses or injuries listed on the questionnaire, and is provided an area where the user may enter additional information concerning specific injuries or illnesses. Accordingly, this medical questionnaire may be a typical medical questionnaire.

While the medical questionnaire in the screen display 2200 is in view, (i.e., while the current medical questionnaire is being completed), information may be changed. However, a medical questionnaire may not be updated after it has been completed and accepted. Also, while the medical questionnaire is in view, it may be deleted. After the medical questionnaire has been completed and accepted, the date may be deleted by selecting the date of the medical questionnaire from the region 1404 and by then selecting a Delete date option which appears in a resulting overlay. A medical questionnaire may be printed before it is accepted.

However, once the medical questionnaire has been accepted, it may not be printed because it is stored outside of the data processing system 100.

From the employee record in the screen display 1400, new requests for medical clearance can be added by activating the button 1406, and existing clearance records may be accessed from the region 1408. If desired, the most recent medical clearance records for each person also can be accessed from the "go to related" portions of a medical evaluation requirements screen display and the request for medical clearance form screen display. The requests for medical clearances may also be accessed through the View Respirator Program button 1708 and the Audit Preparation button 1712.

An example of a request for medical clearance is shown in FIG. 23 as a screen display 2300. The request is necessary in order to clear the use by the employee of one or more respirators. This screen display 2300 includes the name of the employee for whom medical clearance is requested, the employee's identification number, the date of the request, the birth date of the employee, the employee's supervisor and department, the type or types of respirators to be used by the employee, and the level of work effort to be expended by the employee during the job for which each designated respirator is to be used. By accessing additional pages of the request for medical clearance through the use of buttons similar to a button 2302, the user may provide such other information as the extent of the usage of a respirator, the length of continuous time that a respirator will be used, any special work considerations required for a particular job, the name of a safety representative, any restrictions imposed by a physician on the use of a respirator by the employee, the nature of the restrictions, and the name of the physician imposing the restrictions. As shown by the screen display 2300, records related to requests for medical clearance may be deleted and/or printed.

Qualitative and quantitative fit test records are also linked to the employee by the screen display 1400. For example, to access qualitative and/or quantitative fit test records from the screen display 1400, a user may highlight a respirator displayed within the region 1412 of the screen display 1400 and may then press the enter key which causes a screen display 2400 as shown in FIG. 24 to be presented. The name of the employee and the respirator type are inserted by the respirator program 118 into the screen display 2400 based upon the employee name and respirator type selected from the screen display 1400. The dates of fit tests for an employee/respirator combination are provided in a region 2402 of screen display 2400. An existing fit test record may be accessed by selecting a fit test record displayed in the region 2402. Also, a new fit test record may be added by selecting a button 2404 of the screen display 2400.

When the button 2404 is selected, the user is requested to indicate the type of fit test record which is to be created, i.e. a qualitative fit test record or a quantitative fit test record. If a qualitative fit test record is requested, a screen display 2500 shown in FIG. 25 is presented to the user. This screen display includes the name and employee identification for a specific employee, the type of respirator involved in the qualitative fit test, and the date of the qualitative fit test record. The user may enter the size of the respirator involved in the qualitative fit test, the respiratory hazards against which the fit test was made, and the results of tests of the respirator involving certain contaminants. By accessing additional pages of the qualitative fit test through the use of buttons similar to a button 2502, the user provides such other information as the results of tests of the respirator involving certain other contaminants, comments in a comment section, a date by which the fit test must be repeated, and the name of the person conducting the fit test.

A quantitative fit test record may also be generated by activating the button 2404 of the screen display 2400, and choosing the quantitative record option thereby causing a screen display 2600 as shown in FIG. 26 to be presented to the user. As shown in FIG. 26, the screen display 2600 includes the name and employee identification number of the employee, the type of respirator involved in the quantitative fit test, and the date on which the quantitative fit test was conducted. The user may enter the size of the respirator involved in the quantitative fit test, the respiratory hazards encountered during the quantitative fit test, an indication of whether the employee passed the quantitative fit test and the level at which the employee passed, and an indication of the fit factor of the quantitative fit test. By accessing additional pages of the quantitative fit test through the use of buttons similar to a button 2602, the user may provide such other information as the identity of any instrumentation which was used during the test, the identity of a specific probe which was used during the test, comments in a comment section, an indication of where a strip chart record of the test may be found, and the identity of the person who conducted the test.

Training sessions cannot be set up from the screen display 2400. Training sessions are set up from the screen display 500 during development of the workplace respiratory protection program, or from the screen display 1900 as will be discussed hereinafter. When a training session is set up, it is added automatically to a region 2406 of the screen display 2400. Thus, training sessions are displayed in the region 2406 of the screen display 2400.

The user may search for, and thereby access, existing employee records, such as the employee record shown by the screen display 1400 of FIG. 14, by selecting the button 1912 of the screen display 1900. Selecting the button 1912 presents the user with a list of employees. Selection of one of the employees on the list provides the user with the selected employee's record in the form of the screen display 1400 as shown in FIG. 14. From this screen display 1400, the user may process, print, or delete an employee record.

The user may search for, and thereby access, training records by selecting the button 1916 of the screen display 1900. Upon selection of the button 1916, the user is presented with a list of training sessions. After selecting a training session from the list, the user may view an attendance roster in a form similar to the screen display 1600. From this screen display, the records relating to training sessions may be printed and/or deleted. Training session records are also provided in a training appendix of the program which may be accessed by a View Respirator Program button and by a Print Respirator Program button of the screen display 1700 as shown in FIG. 17.

Training sessions may be added by selecting the button 1918 of the screen display 1900. Selection of the button 1918 presents the screen display 1600 to the user. Accordingly, as discussed in connection with FIG. 16, the user may enter employee names in a roster of those employees who are to attend an upcoming training session, and the user may select the respirator for which the training session is to be conducted. Training session records may be changed or deleted.

Buttons 1920 and 1922 of the screen display 1900 allow other workplace records to be found, deleted, and/or added. These other workplace records may include, for example, records related to assessment of exposure of employees to particular contaminants, documentation related to the selection of respirators, records regarding breathing air quality testing, records relating to the evaluation of the respirator program, and/or the like.

Figure 27:
FIG. 27 is a representation of a screen display which is accessed from the screen display of FIG. 19.

Selection of the button 1924 allows the user to view and print the form templates used in the respirator program 118. Selection of the button 1924 presents the user with a screen display 2700 as shown in FIG. 27. Accordingly, the attendance roster form template, an exposure assessment form template, a respirator selection documentation form template, the qualitative and quantitative fit test form templates, the medical questionnaire form template, the request for medical clearance form template, a breathing air quality test form template, and a respirator program evaluation form template may be viewed and/or printed. These templates represent the forms which are discussed above and which are presented to the user during development and maintenance of the workplace respiratory protection program.

Finally, selection of the button 1926 allows the user to jump to the Main Menu presented by the screen display 1700.

Figure 28:
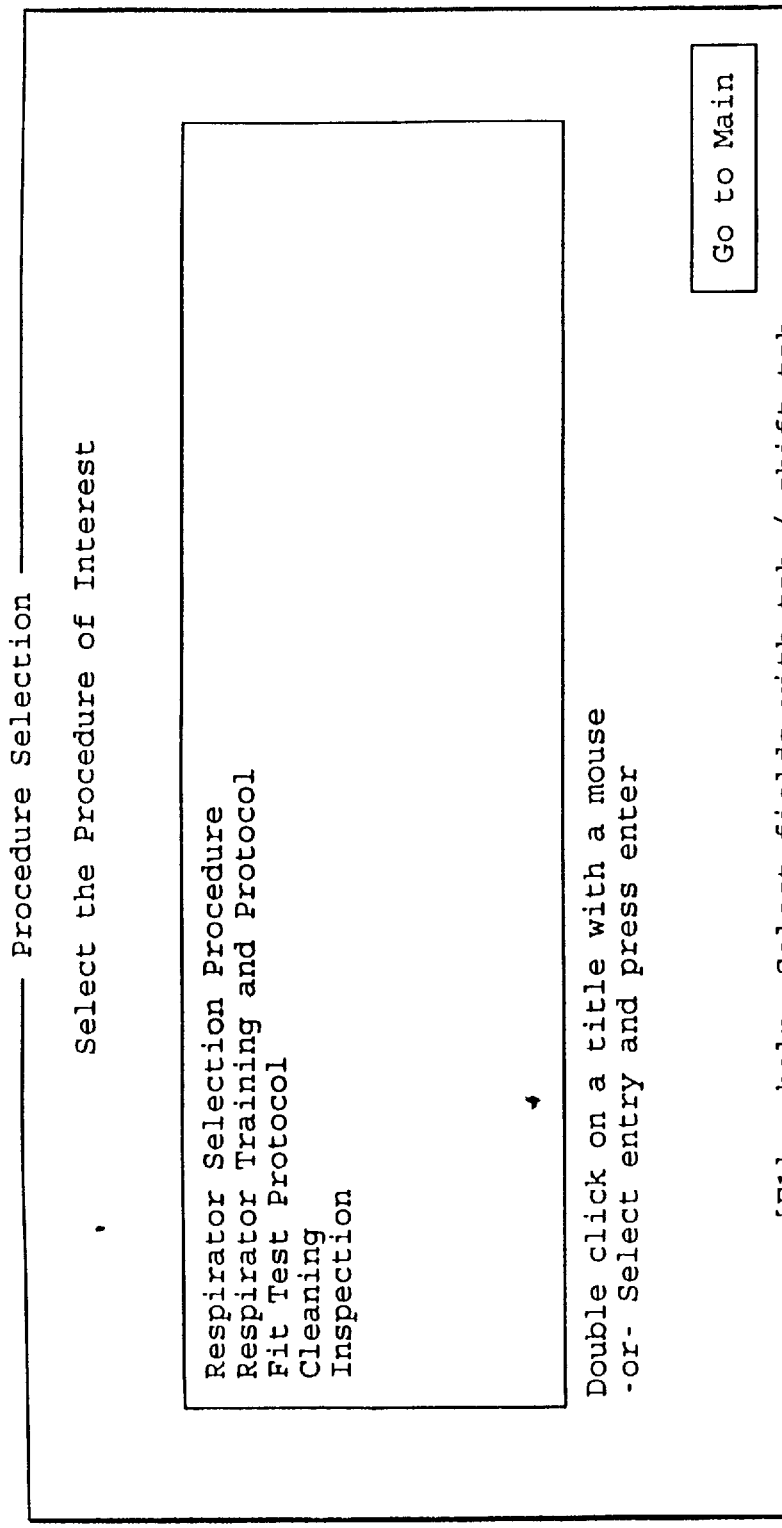
FIG. 28 is a representation of a screen display which is accessed from the screen display of FIG. 17.

Selection of the button 1704 from the screen display 1700 as shown in FIG. 17 permits the user to read/print the standard operating procedures which are incorporated into the respirator program 118. Selection of the button 1704 presents the user with a screen display such as a screen display 2800 as shown in FIG. 28. From this screen display, the user may view the standard operating procedures relating to such aspects of a workplace respiratory protection program as the selection of respirators, the training and protocol related to respirators, the protocols related to fit testing, the procedures related to the cleaning of respirators, and the procedures related to the inspection of respirators. These procedures (i.e., knowledge) may be stored in manual form and may be taken from approved industry recognized procedures, from governmentally recognized procedures relating to the desired topics, and/or from the like.

As indicated by the screen display 2800, these standard operating procedures may be accessed from the screen display 2800. For example, if the standard operating procedures relating to respiratory training and protocol are accessed, these procedures may be similar to those shown in a screen display 2900. The screen display 2900 includes a scrollable window 2902 wherein the standard operating procedures may be read. The screen display 2900 also includes a button 2904 which, when activated, presents an overlay to permit the user through a link or hypertext function to access training requirements, training program attendance roster forms, and training session records. Accordingly, as shown by a screen display 3000 in FIG. 30, this overlay may be in the form of a region 3002 which is an overlay of the screen display 2900 shown in FIG. 29. Also, as shown in connection with the screen display 2900, the standard operating procedures may be printed by selection of a button 2906.

Similarly, if the standard operating procedures relating to respirator selection are selected from the screen display 2800, a Go to Related Item button on the resulting screen display permits the user through a link or hypertext function to access respirator selection requirements, respirator selection documentation forms, respirator selection documentation records, and approved respirator records. If the standard operating procedures relating to fit test protocol are selected from the screen display 2800, a Go to Related Item button on the resulting screen display permits the user through a link or hypertext function to access fit test requirements, qualitative fit test record forms, and fit test records. If the standard operating procedures relating to respirator cleaning are selected from the screen display 2800, a Go to Related Item button on the resulting screen display permits the user through a link or hypertext function to access cleaning requirements. If the standard operating procedures relating to respirator inspection are selected from the screen display 2800, a Go to Related Item button on the resulting screen display permits the user through a link or hypertext function to access inspection requirements.

Figure 31:
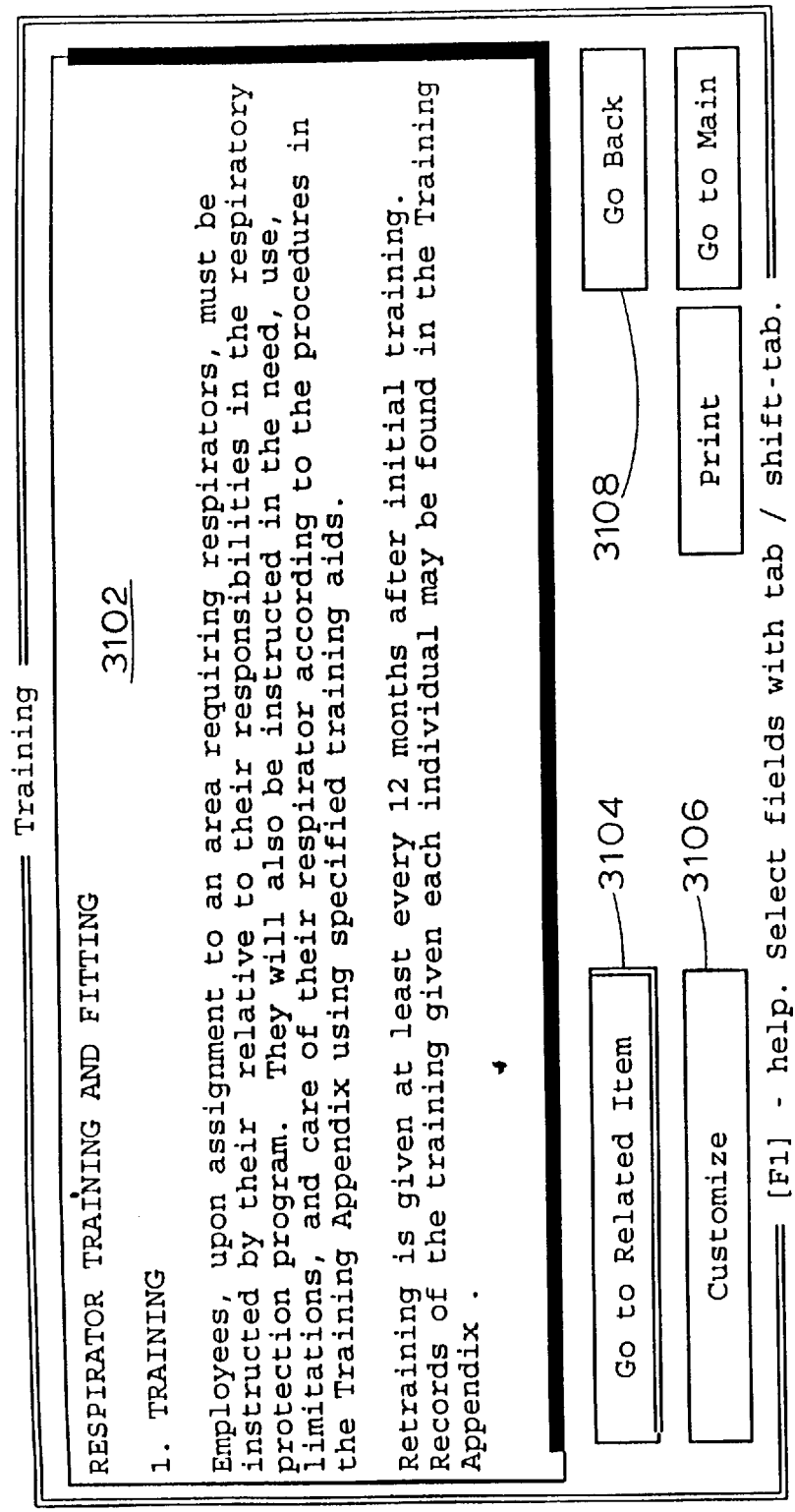
FIG. 31 is a representation of a screen display which is accessed from the screen display of FIG. 30.

Selection of training requirements from the region 3002 of the screen display 3000 may result, for example, in a screen display 3100 as shown in FIG. 31. This screen display 3100 has a scrollable window region 3102 within which the training requirements may be viewed, and a Go to Related Item button 3104 which allows the user through a link or hypertext function to access, for example, the respirator training protocol, the training program attendance roster form, and the training session records. The screen display 3100 also has a Customize button 3106 which allows the user through a link or hypertext function to customize certain information with regard to a training program, such as the title of the employee responsible for instructing employees on respirators and where records regarding the training of each individual employee may be found. A Go Back button 3108 takes the user back to the screen display 2900.

Figure 32:
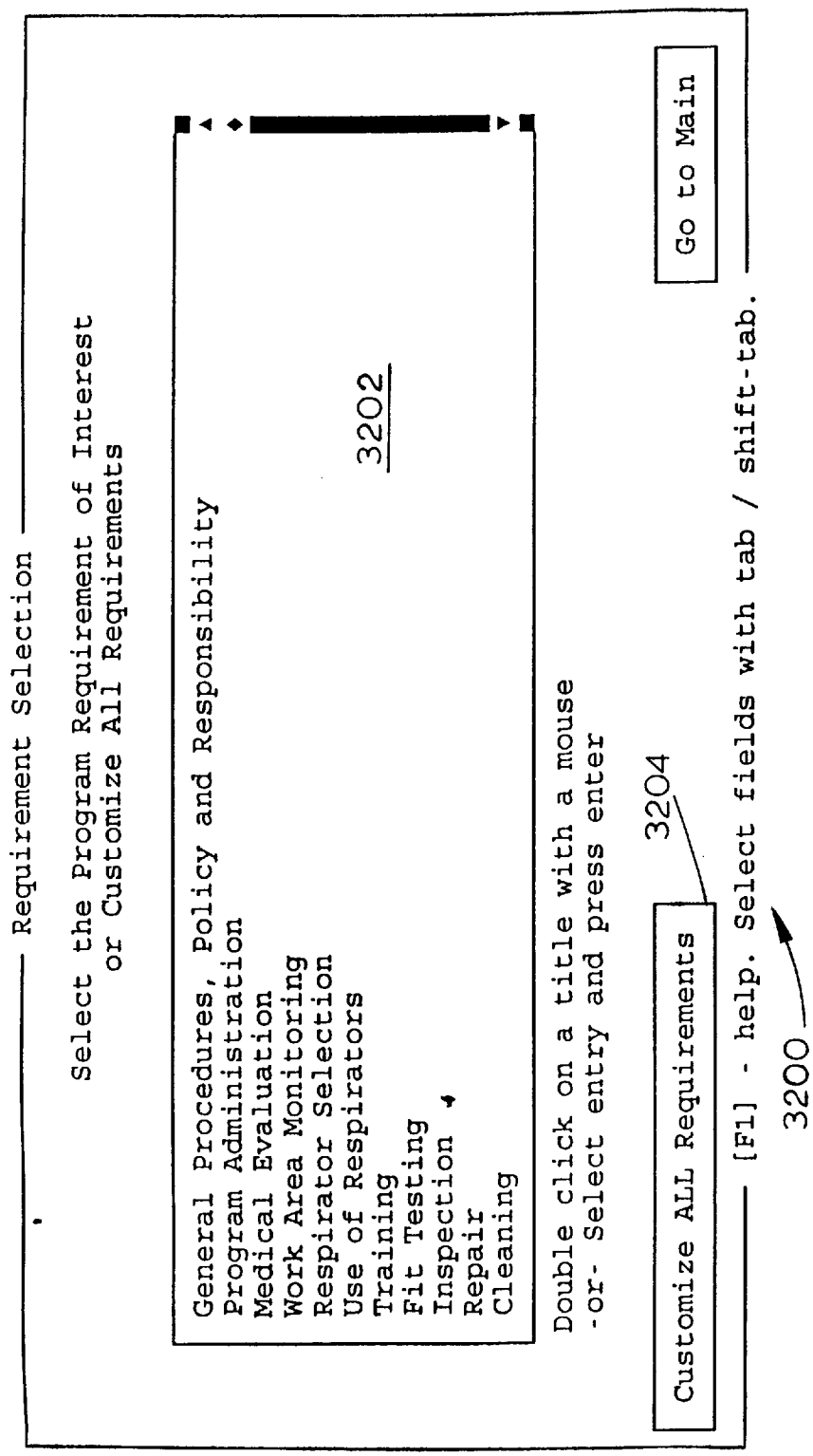
FIG. 32 is a representation of a screen display which is accessed from the screen display of FIG. 17.

Respirator program requirements may be accessed through selection of the button 1706 from the screen display 1700. Selection of the button 1706 presents the screen display 3200 shown in FIG. 32. This screen display allows the user to view requirements related to the workplace respiratory protection program such as the program's general procedures, program administration, medical evaluation, work area monitoring, respirator selection, and the like. In addition to the items shown in the screen display 3200, procedures relating to the storage of respirators and the evaluation of the workplace respiratory protection program may also be accessed. Furthermore, a button 3204 allows customization of all requirements. As discussed above, customization may allow the user to enter the company name of the employer relating to the workplace respiratory protection program, the address of the company, the name and titles of individuals responsible for the various implementation of the requirements, and the like.

Selection of the button 1708 from the screen display 1700 shown in FIG. 17 allows the user to view the respiratory program by paging through information and knowledge in the form of a manual. This manual is assembled by the respirator program 118 as the workplace respiratory protection program is developed, customized, and maintained by the user. It also provides the user with the pre-entered knowledge which forms the basis of any workplace respiratory protection program. Thus, the manual may contain, for example, a plurality of sections wherein some of the sections have been discussed above. These sections in an exemplary order may include general procedures, policy and responsibilities, program administration, medical evaluation, work area monitoring, respiratory selection, use of respirators, training, fit testing, inspection, repair, cleaning, storage, various medical appendices, exposure assessments, respirator selection, training appendices, fit testing appendices, respirator inspection and cleaning appendices, and/or the like.

Selection of the button 1710 from the screen display 1700 shown in FIG. 17 allows the user to print the respiratory program which the user may view by selection of the button 1708.

Selection of the button 1712 from the screen display 1700 shown in FIG. 17 assists the user in preparing for an audit. Accordingly, selection of the button 1712 presents the user with a screen display 3300 as shown in FIG. 33. From this screen display, the user is reminded of the information likely to be required by an auditor. This information may include, for example, program requirements related to the workplace respiratory protection program as developed by the user and as contained in the respirator program 118, records relating to the most recent requests for medical clearances, training protocol, attendance rosters, qualitative fit tests protocols, fit test records, breathing air quality records, and program evaluation records. The user may view and/or print any of this information, as desired, by selecting the item and by then selecting a View and/or Print button.

Selection of the button 1714 from the screen display 1700 as shown in FIG. 17 presents the user with certain miscellany which may include, for example, printer set up, screen colors, importation of employee names, database maintenance, mouse sensitivity, program configuration, and/or the like.

The flow chart of the respirator program 118 is shown in FIGS. 34–40. Since the flow of relevant portions of the respirator program 118 has been described in detail above in connection with FIGS. 2–33, the flow chart shown in FIGS. 34–40 will be only briefly described hereinafter.

When the respirator program 118 is first entered, a block of code 3402 causes the welcome screen 200 to be displayed. If, as indicated by a block 3404, the user elects not to continue, the respirator program 118 is exited. However, if the user elects to continue execution of the respirator program 118, a block 3406 causes the screen display 300 to be displayed. If, as indicated by a block 3408, the user desires help in getting started, a block 3410 causes the screen display 400 to be displayed. As the user reads the screen display 400, the respirator program 118 remains in a wait mode. When the user indicates that it is OK to proceed with the development of a workplace respiratory protection program, a block 3412 causes the screen display 500 to be displayed.

Figure 35:
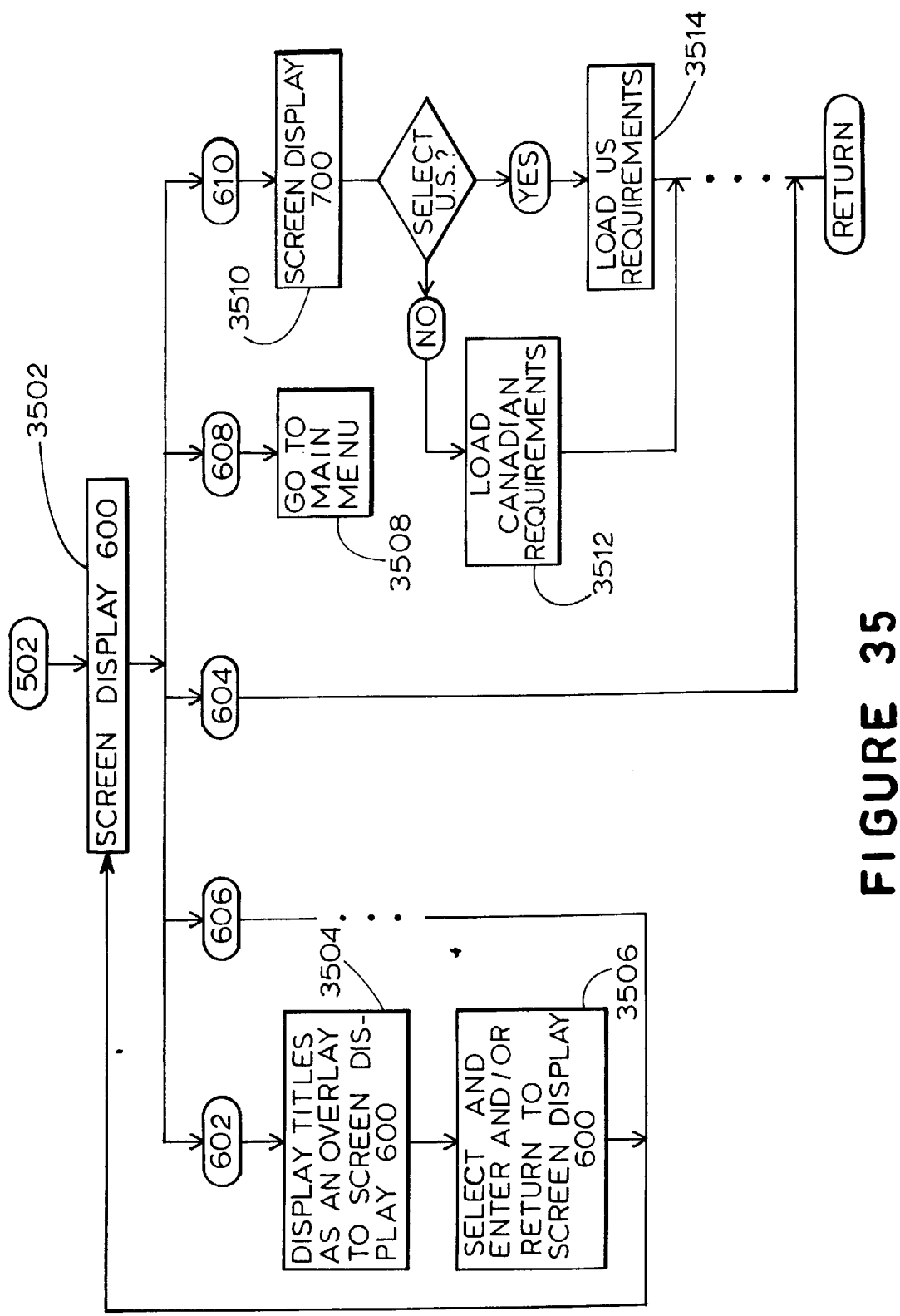

If the user selects the button 502 from the screen display 500, a block 3502 as shown in FIG. 35 causes the screen display 600 to be displayed in order to begin the process of customization. The user may enter, into this screen display 600, the name and address of the company (i.e., employer) for which the workplace respiratory protection program is being developed. If the user selects the button 602 of the screen display 600, a block 3504 causes representative titles to appear, and a block 3506 permits the user to select one of these titles for the named persons.

If the button 604 is selected, the respirator program 118 returns the user to the screen display 500. If the button 606 is selected, the respirator program 118 causes printing of the current screen display 600, a group of screen displays, or all of the customization screen displays involved in the customization of the workplace respiratory protection program. If the button 608 is selected, a block 3508 returns the user to the Main Menu of the screen display 1700. If the button 610 is selected, a block 3510 causes the screen display 700 to be displayed so that the user can enter further customization information. If the user elects to develop the workplace respiratory protection program for Canada, for example, a block 3512 loads Canadian requirements so that the knowledge provided to the user by the respirator program 118 during the development and maintenance of the workplace respiratory protection program is tailored to Canadian requirements. On the other hand, if the user elects to develop the workplace respiratory protection program for the U.S., for example, a block 3514 loads the U.S. requirements so that the knowledge provided to the user by the respirator program 118 during the development and maintenance of the workplace respiratory protection program is tailored to U.S. requirements. Customization may be continued until the user indicates that the customization process is done after which the respirator program 118 returns the user to the screen display 500.

Figure 36:
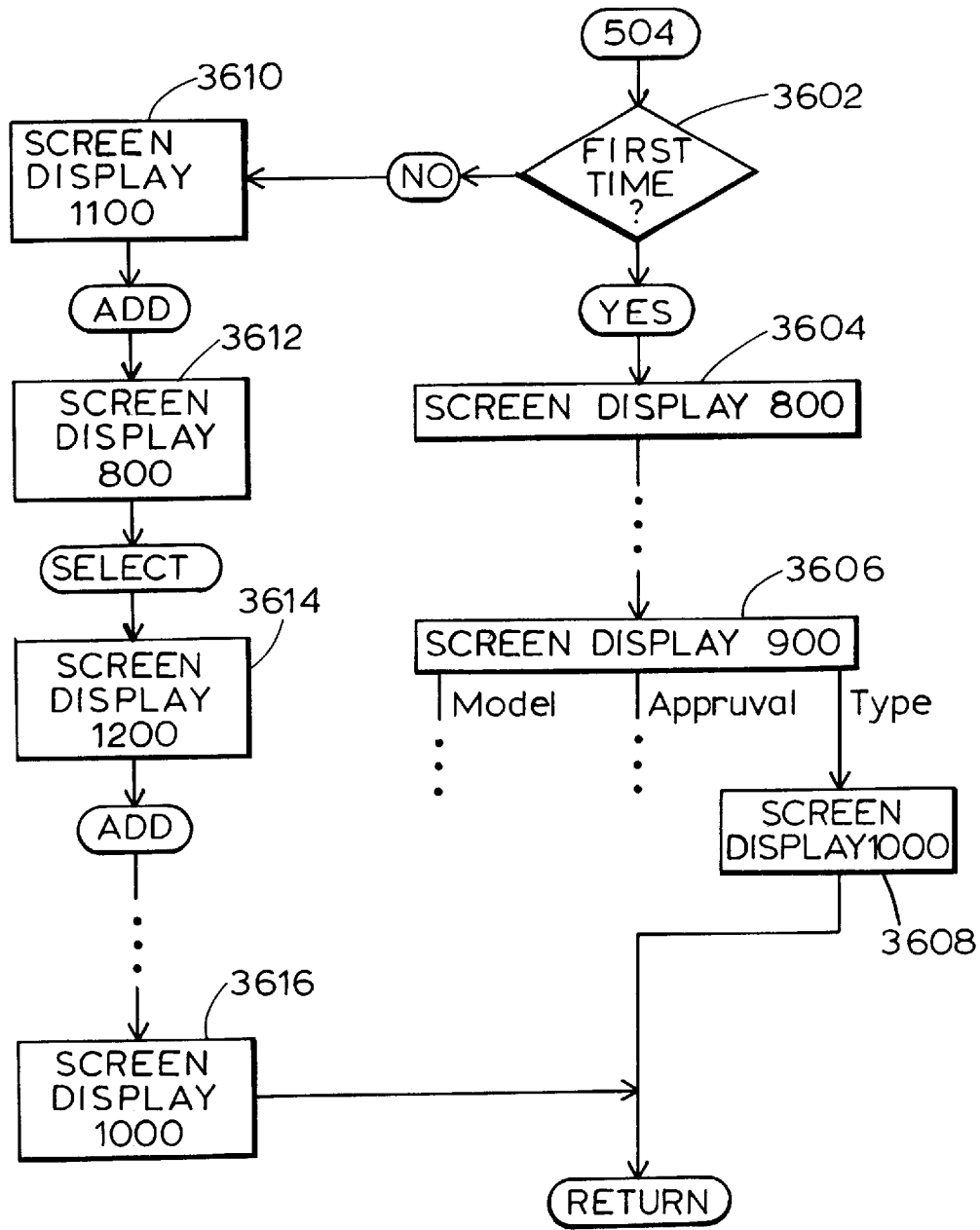

If the button 504 is selected from the screen display 500, a block 3602 as shown in FIG. 36 determines whether a respirator is being selected for the first time. If so, a block 3604 causes the screen display 800 to be displayed to the user. Following completion of the screen display 800 and any subsequent screen displays as described above, a block 3606 causes the screen display 900 to be presented to the user.

If the user requests that the respirators be sorted by type, a block 3608 causes the screen display 1000 to be presented to the user. After the user selects a respirator from the screen display 1000, the respirator program 118 returns the user to the screen display 500.

On the other hand, if a respirator is not being selected for the first time, a block 3610 causes the screen display 1100 to be displayed to the user so that additional respirators may be selected. If the user elects to add a location in which a respirator can be used, a block 3612 causes the screen display 800 to be displayed to the user so that the user may specify the location to be added. After selection of a location, a block 3614 causes the screen display 1200 to be displayed to the user. This process of selecting a new respirator is continued until a block 3616 causes the screen display 900 to be displayed which permits the user to select the new respirator. After the new respirator is selected, the respirator program 118 returns the user to the screen display 500.

Figure 37:
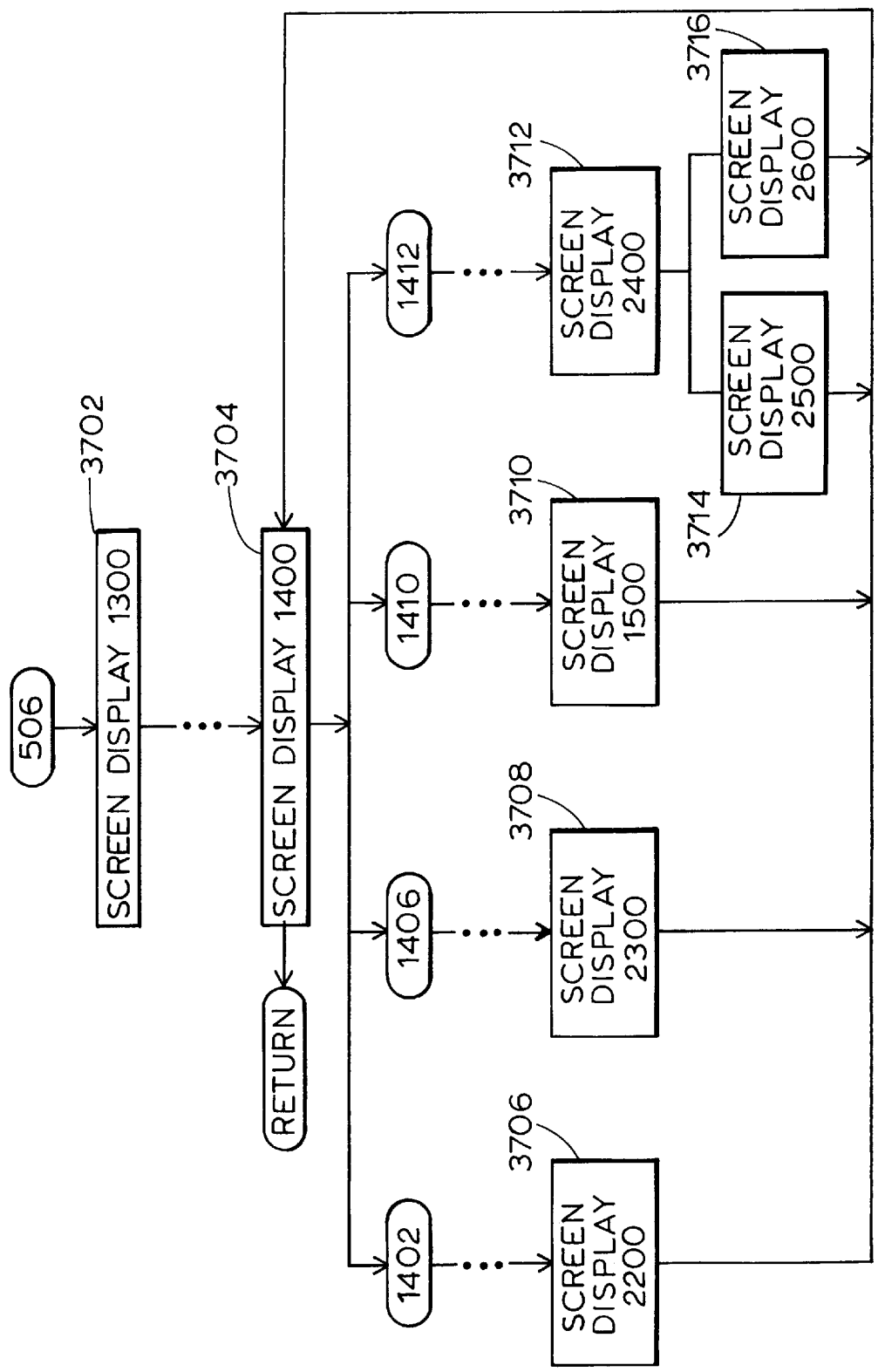

If the button 506 is selected from the screen display 500, a block 3702 as shown in FIG. 37 causes the screen display 1300 to be displayed to the user. After the user enters the name and identification of an employee, a block 3704 causes the screen display 1400 to be displayed to the user so that the user may create a record concerning the identified employee.

Accordingly, if the button 1402 is selected, a block 3706 causes the screen display 2200 to be displayed so that the user can fill out a medical questionnaire about the employee. If the button 1406 is selected, a block 3708 causes the screen display 2300 to be displayed so that the user can fill out a medical clearance form for the employee. If the button 1410 is selected, a block 3710 causes the screen display 1500 to be displayed so that the user may select respirators for the employee. If the button 1412 is selected, a block 3712 causes the screen display 2400 to be displayed so that the user may view and/or add fit tests and view training sessions for the employee. If the user elects to add fit tests from the screen display 2400, a block 3714 causes the screen display 2500 to be displayed to the user, and a block 3716 causes the screen display 2600 to be displayed to the user. After completion of the screen display 1400, the respirator program 118 returns the user to the screen display 500.

Figure 38:
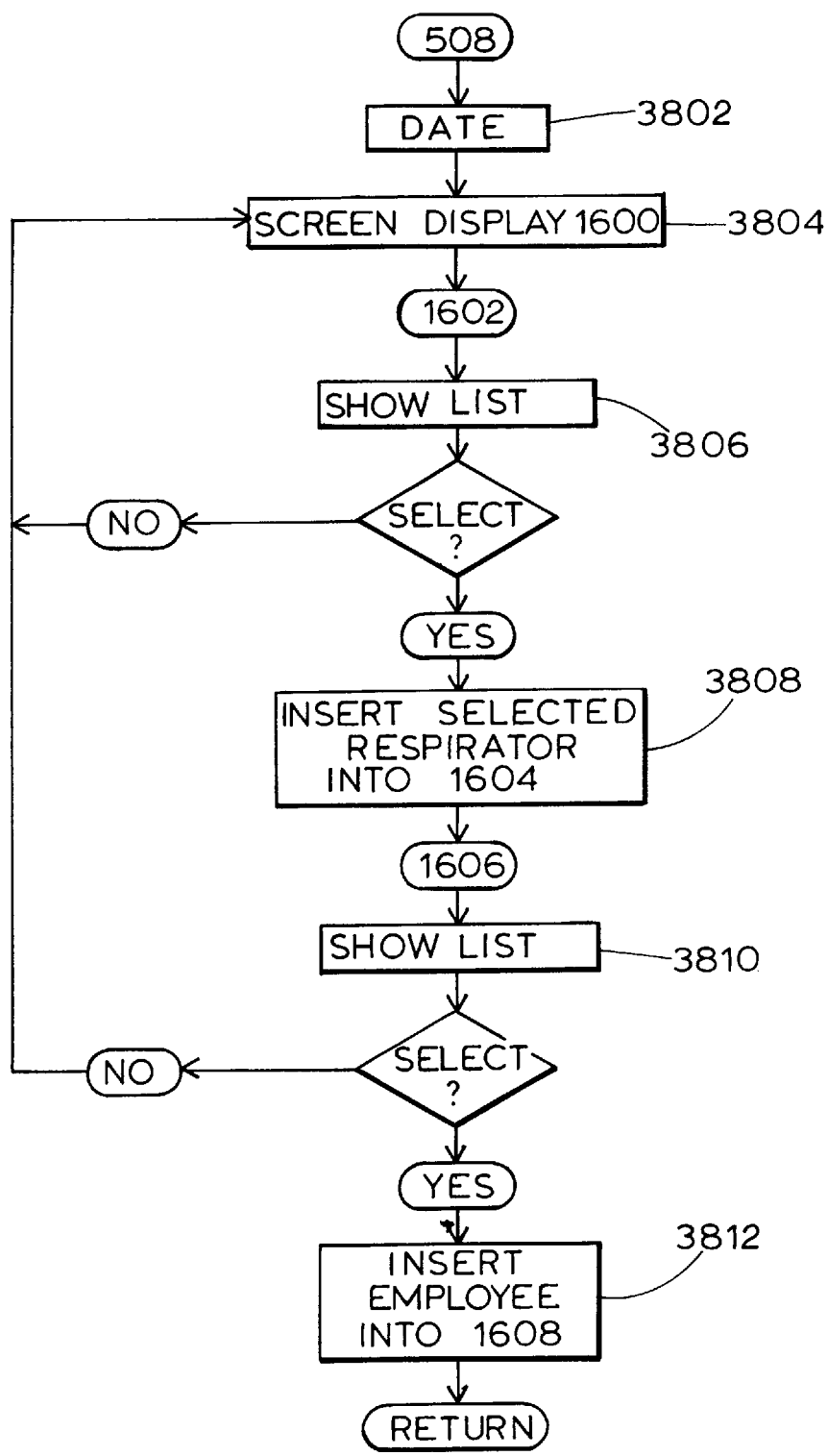

If the button 508 is selected from the screen display 500, a block 3802 as shown in FIG. 38 causes a screen display to be displayed in which the user is asked to insert a date on which a respirator training session is to be conducted. Thereafter, a block 3804 causes the screen display 1600 to be displayed to the user. When the button 1602 is selected by the user, a block 3806 causes a list of respirators to be displayed to the user. If the user selects a respirator from this list, a block 3808 causes the selected respirator to be inserted into the region 1604 of the screen display 1600.

When the button 1606 is selected, a block 3810 causes a list of employees to be displayed to the user. If the user selects an employee from this list, a block 3812 causes the name of the selected employee to be inserted into the scrollable region 1608 of the screen display 1600. Thereafter, as shown in FIG. 38, the respirator program 118 returns the user to the screen display 500.

Figure 34:
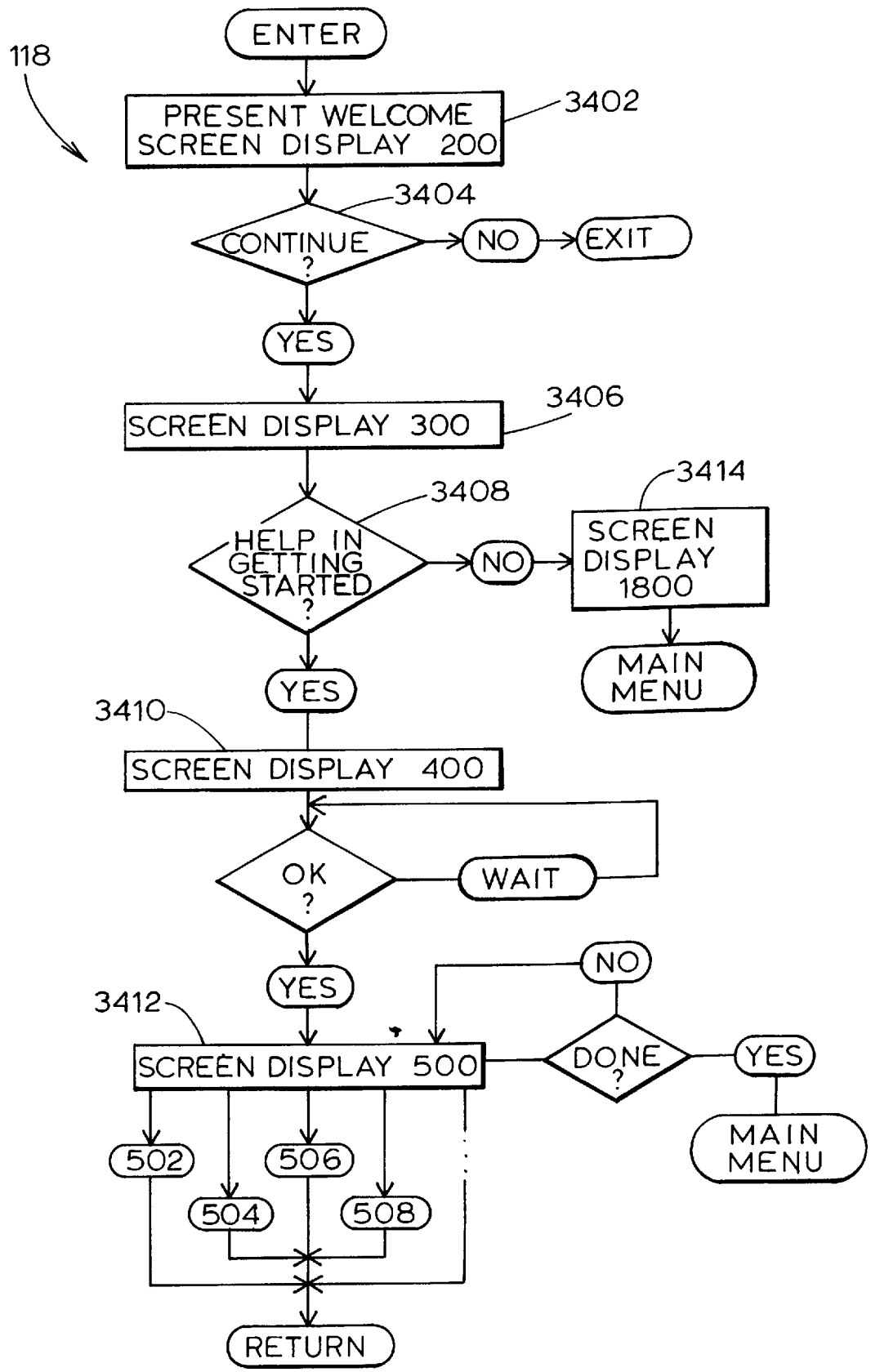
FIGS. 34–40 show a flow chart of the respirator program according to the present invention; and, FIG. 41 is a representation of a screen display which is accessed from the screen display of FIG. 30.

As shown in FIG. 34, if the user declines help in getting started (e.g., the user has already initially developed the workplace respiratory protection program), a block 3414 causes the screen display 1800 to be displayed to the user to remind the user of any tasks which must be done. Thereafter, the Main Menu is entered. Also as shown in FIG. 34, the Main Menu is entered after the workplace respiratory protection program has been developed from the screen display 500.

Figure 39:
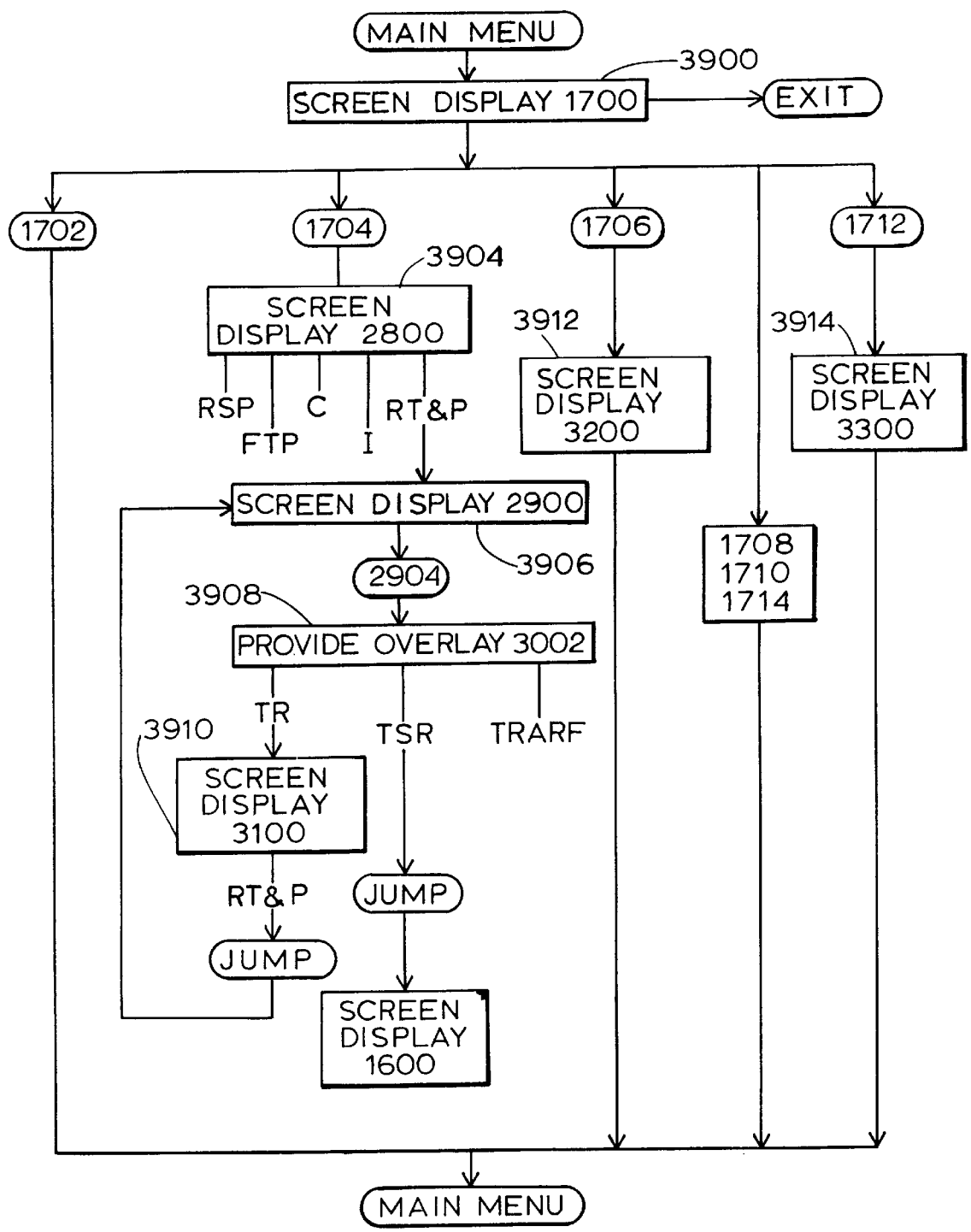
Figure 40:
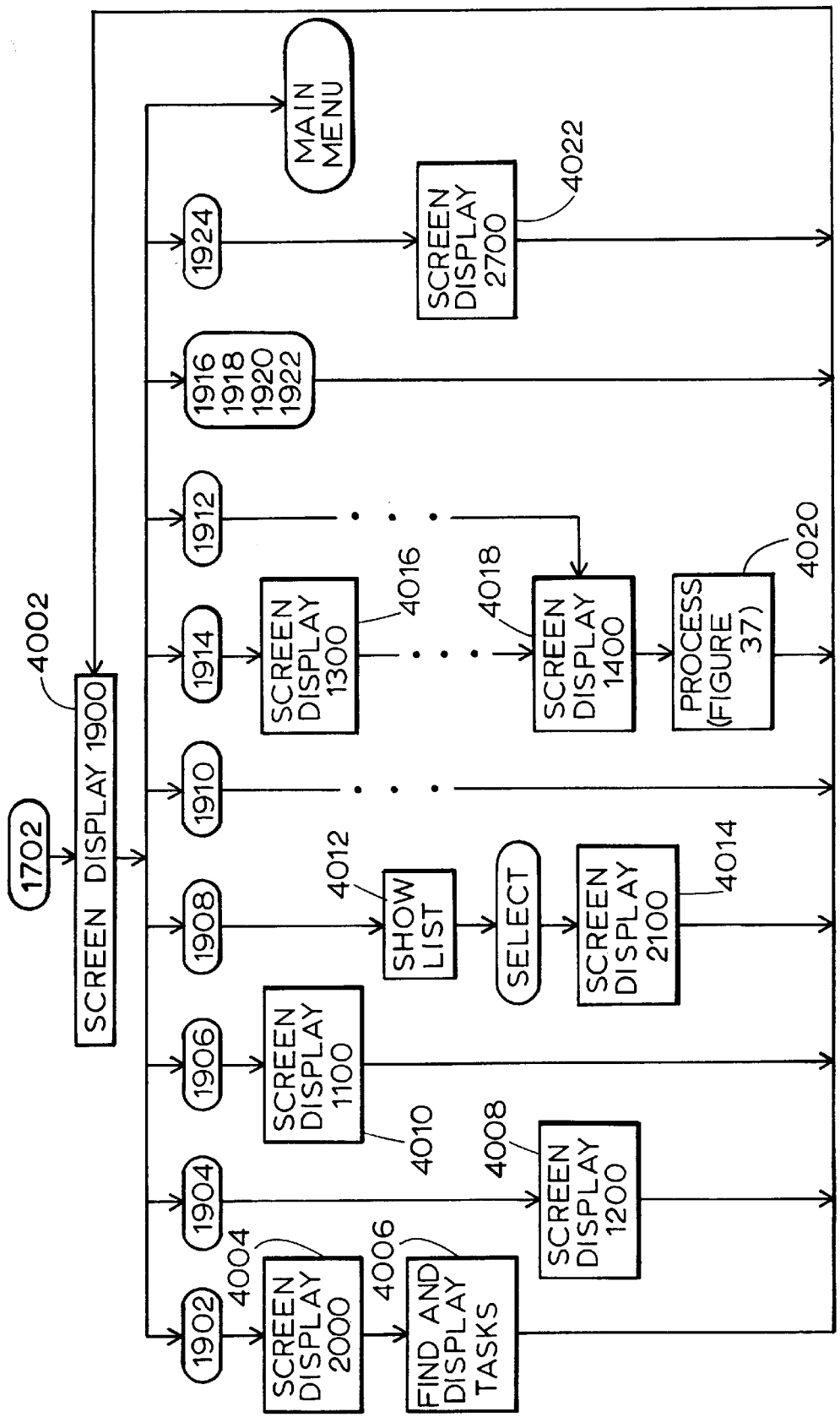

When the Main Menu is entered, a block 3900 as shown in FIG. 39 causes the screen display 1700 to be displayed to the user. If the button 1702 is selected from the screen display 1700, a block 4002 as shown in FIG. 40 causes the screen display 1900 to be displayed to the user. If the user selects the button 1902 from the screen display 1900, a block 4004 causes the screen display 2000 to be displayed to the user. By use of the screen display 2000, the user may specify a search time period within which tasks may be due. After the user inserts the number of days into the screen display 2000, a block 4006 finds any tasks due between the current date and the date at the end of the time period specified by the number of days entered into the screen display 2000 by the user and displays those tasks.

If the user selects the button 1904 from the screen display 1900, a block 4008 causes a screen display similar to the screen display 1200 in FIG. 12 to be displayed to the user. By use of this screen display, the user can find current jobs by job title or add new job titles to the current list of jobs.

If the user selects the button 1906 from the screen display 1900, a block 4010 causes a screen display similar to the screen display 1100 in FIG. 11 to be displayed to the user. By use of this screen display, the user can find current locations or add new locations to the current list of locations.

If the user selects the button 1908 from the screen display 1900, a block 4012 causes a list of approved respirators to be displayed to the user. When the user selects a respirator from this list, a block 4014 causes the screen display 2100 to be displayed to the user.

If the user selects the button 1914 from the screen display 1900, a block 4016 causes the screen display 1300 to be displayed to the user. After the user enters the name and identification of an employee, a block 4018 causes the screen display 1400 to be displayed to the user so that the user may enter additional information concerning the employee. A block 4020 then causes that part of FIG. 37 related to the screen display 1400 to be performed.

The user may search for, and thereby access, existing employee records, such as the employee record shown by the screen display 1400 of FIG. 14. This search is initiated by selecting the button 1912 of the screen display 1900. Selecting the button 1912 presents a screen display which provides the user with a list of employees. Following selection of one of the employees on the list, the blocks 4018 and 4020 are performed.

Selecting the button 1910 allows the user to add respirators by location and by job to the list of approved respirators.

Selection of the button 1916 allows the user to view the attendance roster for a selected training session. Selecting the button 1918 allows the user to enter employee names in a roster of those employees who are to attend an upcoming training session, and the user may select the respirator for which the training session is to be conducted. Selection of the buttons 1920 and 1922 allow the user to find and to add other workplace records.

If the user selects the button 1924, a block 4022 causes the screen display 2700 to be displayed to the user. Accordingly, the attendance roster form template, an exposure assessment form template, a respirator selection documentation form template, the qualitative and quantitative fit test form templates, the medical questionnaire form template, the request for medical clearance form template, a breathing air quality test form template, and a respirator program evaluation form template may be viewed and/or printed.

If the user selects the button 1704 from the screen display 1700, a block 3904 causes the screen display 2800 to be displayed to the user. If the standard operating procedures relating to respiratory training and protocol are selected, for example, a block 3906 causes the screen display 2900 to be displayed to the user so that the user may read the standard operating procedures of the workplace respiratory protection program. If the user selects the Go To Related button from the screen display 2900, a block 3908 provides an overlay on the screen display 2900 so that the user, through a link or hypertext function, can access training requirements (TR), training program attendance roster forms (TRARF), and training session records (TSR). If the user selects training requirements, for example, a block 3910 causes the screen display 3100 to be displayed to the user. If the user selects the Go To Related button of the screen display 3100 and selects respirator training and protocol from the resulting overlay, the respirator program 118 jumps through the hypertext link to the screen display 2900 so that the user can view the respirator training and protocol requirements. On the other hand, if the user selects training sessions records from the overlay 3002, the user is presented with a display 4100 as shown in FIG. 41 from which, by the user selecting a training session from a list of training sessions, the respirator program 118 jumps through a hypertext link to the screen display 1600 so that the user can view training sessions records.

If the user selects the button 1706 from the screen display 1700, a block 3912 causes the screen display 3200 to be displayed to the user. This screen display allows the user to view requirements related to the workplace respiratory protection program such as the program's general procedures, program administration, medical evaluation, work area monitoring, respirator selection, procedures relating to the storage of respirators and the evaluation of the workplace respiratory protection program, and the like.

Selection of the button 1708 allows the user to page through information and knowledge in the form of a manual. Selection of the button 1710 allows the user to print the respiratory program which the user may view by selection of the button 1708. If the button 1712 is selected, a block 3914 causes the screen display 3300 to be displayed to the user. From this screen display, the user is reminded of the information likely to be required by an auditor. Selection of the button 1714 presents the user with certain miscellany.

As shown in at least some of the screen displays, the Main Menu may be accessed directly from many of the screen displays. Also, the escape key or other key may be used to return to the screen display from which the current screen display was accessed. Moreover, a key such as the function key F1 may be used to display help information concerning any screen display currently being displayed. The present invention provides multiple views of the same data. For example, respirators selected by job and by location may be displayed in the screen displays 1400, 1500, and 2600. The screen displays shown herein are by way of example only. Other screen displays which implement the present invention are possible. Other alternatives and modifications will occur to those skilled in the art. All such alternatives and modifications are covered by the present invention.

We claim:

1. A computer readable storage medium having program stored thereon, wherein the program code is arranged so that, when the program code is executed by a computer, the following steps are performed:

(a) retrieving requirements of the workplace respiratory protection program from a database and displaying the requirements of the workplace respiratory protection program to a user; and, (b) prompting development of the workplace respiratory protection program based upon the requirements of the workplace respiratory protection program stored in the database and displayed to the user, whereby the user is guided through the development of the workplace respiratory protection program.

2. The computer readable storage medium of claim 1 wherein step (b) comprises the step of executing program code to prompt the development of the workplace respiratory protection program which complies with regulations relating to governmental respiratory protection requirements.

3. The computer readable storage medium of claim 2 wherein step (b) comprises the step of displaying forms useful in the development of the workplace respiratory protection program, and wherein the forms are stored in the database.

4. The computer readable storage medium of claim 3 wherein the forms represent records of data concerning respiratory protection of employees, and wherein step (b) comprises the step of displaying multiple views of the data.

5. The computer readable storage medium of claim 3 wherein the forms include records which are linked to personal IDs of employees by links.

6. The computer readable storage medium of claim 5 wherein step (b) comprises the step of importing employee names and personal IDs from other application programs to the workplace respiratory protection program.

7. The computer readable storage medium of claim 5 wherein the records include respirators linked to individual employees, to fit testing of individual employees, and to training of individual employees.

8. The computer readable storage medium of claim 5 wherein the records include medical questionnaires and requests for medical clearance linked to individual employees.

9. The computer readable storage medium of claim 5 wherein step (b) comprises the step of displaying a screen which permits access to the links.

10. The computer readable storage medium of claim 9 wherein access to at least some links is direct.

11. The computer readable storage medium of claim 1 wherein step (b) comprises the step of displaying forms useful in the development of the workplace respiratory protection program, and wherein the forms are stored in the database.

12. The computer readable storage medium of claim 11 wherein the forms represent records of data concerning respiratory protection of employees, and wherein step (b) comprises the step of displaying multiple views of the data.

13. The computer readable storage medium of claim 11 wherein the forms include records which are linked to personal IDs of employees by links.

14. The computer readable storage medium of claim 13 wherein the records include medical questionnaires and requests for medical clearance linked to individual employees.

15. The computer readable storage medium of claim 13 wherein the records include respirators linked to individual employees, to fit testing of individual employees, and to training of individual employees.

16. The computer readable storage medium of claim 13 wherein step (b) comprises the steps of displaying a screen which permits access to the links.

17. The computer readable storage medium of claim 16 wherein access to at least some links is direct.

18. The computer readable storage medium of claim 1 wherein, when the program code is executed by the computer, the following further step is performed: displaying standard operating procedures relating to the workplace respiratory protection program, wherein the standard operating procedures are stored in the database of the data processing system.

19. A method of developing a workplace respiratory protection program, the method comprising the steps, performed by a data processing system, of:

(a) executing first program code to display customized requirements for a workplace respiratory protection program;

(b) executing second program code in order to display forms useful in the development of the workplace respiratory protection program;

(c) linking the first and second program codes in hypertext fashion; and, (d) modifying the forms to match the customized requirements.

20. The method of claim 19 wherein the forms represent records of data concerning respiratory protection of employees, and wherein the method further comprises the step of executing program code to display multiple views of the data.

21. The method of claim 19 further comprising the step of executing third program code to display standard operating procedures related to the workplace respiratory protection program.

22. The method of claim 21 wherein the step of linking the first and second program codes in hypertext fashion comprises the step of linking the first, second, and third program codes in hypertext fashion.

23. A method of developing a workplace respiratory protection program, the method comprising the steps, performed by a data processing system, of:

(a) executing first program code to retrieve requirements of the workplace respiratory protection program from a database of the data processing system and to display the requirements of the workplace respiratory protection program to a user; and, (b) executing second program code to prompt the development of the workplace respiratory protection program which is based upon the requirements of the workplace respiratory protection program, which guides the user through the development and customization of the workplace respiratory protection program, and which complies with governmental respiratory protection regulations of first and second countries.

24. The method of claim 23 wherein knowledge concerning the governmental respiratory protection regulations of both of the first and second countries is stored in a database of the data processing system.

25. The method of claim 24 further comprising the step of executing third program code to display standard operating procedures relating to the workplace respiratory protection program.

26. The method of claim 23 wherein the step of executing second program code comprises the step of executing program code in order to display forms useful in the development of the workplace respiratory protection program in accordance with the governmental respiratory protection regulations.

27. A computer readable storage medium having program stored thereon, wherein the program code is arranged so that, when the program code is executed by a computer, the following steps are performed:
   (a) prompting customization of workplace respiratory protection requirements of the workplace respiratory protection program, wherein the workplace respiratory protection requirements include employee training and respirator selection data; and,
   (b) displaying forms useful in the customization of the workplace respiratory protection program.

28. The computer readable storage medium of claim 27 wherein, when the program code is executed by the computer, the following further step is performed: displaying standard operating procedures relating to the workplace respiratory protection program.

29. The computer readable storage medium of claim 27 wherein step (a) comprises the step of accessing a database which includes knowledge helpful in the customization of the workplace respiratory protection requirements.

30. The computer readable storage medium of claim 29 wherein the knowledge includes restrictions on the customization of the workplace respiratory protection requirements.

31. The computer readable storage medium of claim 29 wherein the knowledge includes likely optional entries.

32. The computer readable storage medium of claim 29 wherein the knowledge is dependent upon countries for which the workplace respiratory protection program is developed.

33. The computer readable storage medium of claim 29 wherein the knowledge is dependent upon categories of respirators which may be included in the workplace respiratory protection program.

34. The computer readable storage medium of claim 27 wherein step (a) comprises the step of displaying alerts relating to tasks to be done, and wherein the alerts may be customized by execution of the first program code.

35. A method of developing a workplace respiratory protection program and of preparing for an audit thereof, the method comprising the steps, performed by a data processing system, of:
   (a) executing first program code to prompt the development of a workplace respiratory protection program which complies with governmental respiratory protection regulations; and,
   (b) executing second program code in order to prompt a user in preparing for an audit of the workplace respiratory protection program by displaying customized regulations linking program customization and maintenance information likely to be requested by an auditor, wherein the execution of the second program code includes displaying to the user a form reminding the user of the information likely to be required by the auditor.

36. The method of claim 35 wherein step (a) comprises the step of executing program code to provide knowledge most likely to be requested by an auditor.

37. The method of claim 36 wherein the step of executing program code to provide knowledge most likely to be requested by an auditor comprises the step of providing access to this knowledge from a single screen display.

38. A computer readable storage medium having program stored thereon, wherein the program code is arranged so that, when the program code is executed by a computer, the following steps are performed:
   (a) prompting development of a workplace respiratory protection program which includes respiratory protection requirements and creation of records; and,
   (b) prompting maintenance of the workplace respiratory protection program so as to stay in compliance with the respiratory protection requirements by alerting a user to tasks which are due or have not been completed.

39. The computer readable storage medium of claim 38 wherein, when the program code is executed by the computer, the following further step is performed: integrating the first and second program codes through a single screen display.

40. A computer readable storage medium having program stored thereon, wherein the program code is arranged so that, when the program code is executed by a computer, the following steps are performed:
   (a) prompting maintenance of a workplace respiratory protection program so as to stay in compliance with regulations relating to governmental respiratory protection requirements by alerting a user to tasks which are due or have not been completed; and,
   (b) in response to step (a), displaying forms useful in the maintenance of the workplace respiratory protection program.

41. The computer readable storage medium of claim 40 wherein, when the program code is executed by the computer, the following further step is performed: displaying alerts relating to tasks to be done.

42. The computer readable storage medium of claim 41 wherein the step of displaying alerts comprises the step of displaying the alerts at log on.

43. The computer readable storage medium of claim 42 wherein the step of executing program code to display alerts comprises the steps of displaying the alerts dependent upon constraints and changing the constraints.

44. The computer readable storage medium of claim 41 wherein the step of executing program code to display alerts comprises the step of displaying the alerts upon request.

45. The computer readable storage medium of claim 44 wherein the step of executing program code to display alerts comprises the steps of displaying the alerts dependent upon constraints and changing the constraints.

46. The computer readable storage medium of claim 44 wherein the step of executing program code to display alerts comprises the step of displaying the alerts at log on.

47. A method of maintaining a workplace respiratory protection program and of preparing for an audit thereof, the method comprising the steps, performed by a data processing system, of:
   (a) executing first program code to maintain records relating to the workplace respiratory protection program; and,
   (b) executing second program code in order to assist a user in preparing for an audit of the workplace respiratory protection program by displaying customized regulations linking program customization and maintenance information which may be requested by an auditor, wherein the execution of the second program code includes displaying to the user a form reminding the user of the information likely to be required by the auditor.

48. The method of claim 47 wherein the step of executing the second program code comprises the step of executing program code to provide knowledge most likely to be requested by an auditor.

49. The method of claim 48 wherein the step of executing program code to provide knowledge most likely to be requested by an auditor comprises the step of providing access to this knowledge from a single screen display.

50. The method of claim 48 wherein the knowledge most likely to be requested by an auditor is based upon the records.

51. A method of maintaining a workplace respiratory protection program, the method comprising the steps, performed by a data processing system, of:
   (a) executing program code to maintain records concerning the workplace respiratory protection program to enable an employer to stay in compliance with respiratory protection requirements; and,
   (b) executing program code to display a linking screen containing a personal ID of an employee, a respirator associated with the employee, a training link to a training requirement for an employee/respirator combination, and a fit test link to a fit test record for the employee/respirator combination.

52. The method of claim 51 wherein the step of executing program code to maintain records concerning the workplace respiratory protection program comprises the step of executing program code to maintain records relating to respirators associated with employees, to training requirements for employees, and to fit testing of employees.

53. The method of claim 51 wherein the step of executing program code to display a linking screen comprises the step of executing program code to display a linking screen containing a respirator associated with the employee, a training link to a training requirement for the employee, and a fit test link to a fit test record for the employee.

54. The method of claim 51 wherein the step of executing program code to maintain records concerning the workplace respiratory protection program comprises the step of executing program code to maintain records relating to exposure assessments, to medical questionnaires, to requests for medical clearance, to breathing air quality test, and to respirator program evaluations.

55. A computer readable storage medium having program stored thereon, wherein the program code is arranged so that, when the program code is executed by a computer, the following steps are performed:
   (a) maintaining training records and fit testing records for the workplace respiratory protection program; and,
   (b) accessing the records through links, wherein the training records and fit testing records are linked to a respirator.

56. The computer readable storage medium of claim 55 wherein step (b) comprises the step of accessing records which include a location for the respirator, a job for which the respirator may be used, and standard operating procedures related to the respirator.

57. The computer readable storage medium of claim 56 wherein the standard operating procedures include cleaning and inspection procedures for the respirator.

58. A computer readable storage medium having program code stored thereon, wherein the program code is arranged so that, when the program code is executed by a computer, the following steps are performed:
   (a) prompting development by a user of a workplace respiratory protection program, wherein the prompting of the workplace respiratory protection program is based upon governmental workplace respiratory protection requirements; and,
   (b) executing program code to prepare a manual in a database of the data processing system, wherein the manual includes the workplace respiratory protection program developed by the user, and wherein the manual meets the governmental workplace respiratory protection requirements for a workplace respiratory protection program.

* * * * *

UNITED STATES PATENT AND TRADEMARK OFFICE
CERTIFICATE OF CORRECTION

PATENT NO. : 5,893,070
DATED : April 6, 1999
INVENTOR(S) : Garber et al.

It is certified that error appears in the above-identified patent and that said Letters Patent is hereby corrected as shown below:

<u>Title page,</u>
Item [21], "659,022" should read -- 08/659,022 --.

Item [56], OTHER PUBLICATIONS, sixth cited document, "Acc. No. 0211899;" should read -- Acc. No. 02118997; --

<u>Column 12,</u>
Line 25, "readprint" should read -- read/print --.

Signed and Sealed this

Fourteenth Day of May, 2002

Attest:

JAMES E. ROGAN
Attesting Officer
Director of the United States Patent and Trademark Office